US008158216B2

(12) United States Patent
Thomas et al.

(10) Patent No.: US 8,158,216 B2
(45) Date of Patent: Apr. 17, 2012

(54) SPINULOSE TITANIUM NANOPARTICULATE SURFACES

(75) Inventors: Christina Kay Thomas, St. Paul, MN (US); Luke J. Ryves, Minneapolis, MN (US); Daniel M. Storey, Minneapolis, MN (US)

(73) Assignee: Metascape LLC, Maple Grove, MN (US)

( * ) Notice: Subject to any disclaimer, the term of this patent is extended or adjusted under 35 U.S.C. 154(b) by 995 days.

(21) Appl. No.: 11/932,831

(22) Filed: Oct. 31, 2007

(65) Prior Publication Data

US 2011/0003172 A1 Jan. 6, 2011

(51) Int. Cl.
*H05H 1/24* (2006.01)
(52) U.S. Cl. ........ 427/576; 427/455; 427/569; 427/580; 427/250; 427/248.1
(58) Field of Classification Search ........................ None
See application file for complete search history.

(56) References Cited

U.S. PATENT DOCUMENTS

| 4,955,135 | A | | 9/1990 | Pinkhasov |
| 5,665,326 | A | | 9/1997 | Goel et al. |
| 5,726,524 | A | * | 3/1998 | Debe ............................. 313/309 |
| 5,750,206 | A | | 5/1998 | Hergenrother et al. |
| 6,063,314 | A | | 5/2000 | Chadwick |
| 6,099,939 | A | | 8/2000 | Mittal et al. |
| 6,132,805 | A | * | 10/2000 | Moslehi ..................... 427/248.1 |
| 6,206,065 | B1 | | 3/2001 | Robbie et al. |
| 6,235,361 | B1 | | 5/2001 | Jacquemet et al. |
| 6,248,422 | B1 | | 6/2001 | Robbie et al. |
| 6,306,734 | B1 | | 10/2001 | Givargizov |
| 6,319,369 | B1 | * | 11/2001 | Flynn et al. ............... 204/192.38 |
| 6,506,314 | B1 | | 1/2003 | Whitney, Jr. et al. |
| 6,521,106 | B1 | * | 2/2003 | Actor et al. ............... 204/298.11 |
| 6,752,878 | B2 | | 6/2004 | Montano et al. |
| 6,958,169 | B2 | | 10/2005 | Kunzler et al. |
| 7,186,305 | B2 | | 3/2007 | Ferrier |
| 2003/0136660 | A1 | * | 7/2003 | Gnade et al. ................. 204/164 |
| 2004/0071983 | A1 | | 4/2004 | Manfre et al. |
| 2004/0164281 | A1 | * | 8/2004 | Abe et al. ..................... 252/500 |
| 2004/0228898 | A1 | | 11/2004 | Ross et al. |
| 2006/0193887 | A1 | | 8/2006 | Owens et al. |
| 2007/0018139 | A1 | | 1/2007 | Chandran |

(Continued)

FOREIGN PATENT DOCUMENTS

WO WO 95/04839 2/1995

OTHER PUBLICATIONS

Billinger, M. et al. "Polymer Stent Coating for Prevention of Neointimal Hyperplasia", *J. Invasive Cardiology*, vol. 18, No. 9, pp. 423-426 (2003).

(Continued)

*Primary Examiner* — David Turocy
*Assistant Examiner* — Joel Horning
(74) *Attorney, Agent, or Firm* — Saliwanchik, Lloyd & Eisenschenk

(57) ABSTRACT

Vapor plasma deposition of titanium (Ti) metal onto a substrate forms a structured surface that exhibits enhanced cell attachment properties. Initially deposited round nanoparticulate surface structures develop tentacles with a spine or thorn-like appearance upon continued deposition under special conditions. The density and size of the formed spinulose particles can be controlled by timing the deposition intervals. A significant increase in osteoblast, fibroblast and endothelial cell attachment is observed on Ti spinulose surfaces compared to attachment on nanoparticulate surfaces lacking spinulous nanostructure.

14 Claims, 21 Drawing Sheets

U.S. PATENT DOCUMENTS

2007/0071879 A1    3/2007    Rypacek et al.

OTHER PUBLICATIONS

Brett, Michael J. et al. "New Materials at a Glance," *Science*, vol. 319, pp. 1192-1193 (Feb. 29, 2008).

Kumar, V.R. and Fradeep, T. "Polmerization of benzylthiocyanate on silver nanoparticies and the formation of polymer coated nanoparticles," *J. Mater. Chem.*, vol. 16, pp. 837-841 (2006).

Hawkeye, M.M. & Brfett, M.J., "Glancing Angle Deposition: Fabrication, Properties, and Applications of Micro-And Nanostructured Thin Films," *J. Vac. Sci. Technol.*, Sep./Oct. 2007, pp. 1317-1335, vol. 25, No. 5.

Suzuki, M., Nagai, K., Kinoshita, S., Nakajima, K., Kimura, K., Okano T. & Sasakawa, K., "Vapor Phase Growth of Al Whiskers Induced by Glancing Angle Deposition At High Temperature," *Applied Physics Letters*, 2006, p. 133103, vol. 89.

Wu, C., Li, S., Sassa, K., Sakka, Y., Suzuki, T.S., & Asai, S., "The Crystal Orientation Taking Account of Gravity Force Under High Magnetic Field," *ISIJ International*, 2005, pp. 997-1000, vol. 45, No. 7.

Barsoum, M.W., Hoffman, E.N., Doherty, R.D., Gupta, S. & Zavaliangos, A., "Driving Force and Mechanism for Spontaneous Metal Whisker Formation," *Physical Review Letters*, Nov. 12, 2004, p. 206104, vol. 93, No. 20.

McIntosh, A. Cut, Y., Robertson, M., Robbie, K., & Riehle, M., "Biocompatibility of Glancing Angle Deposited Thin Nanostructured Silicon Films: Relevance of Angle for Fibroblast Reaction," *European Cells and Materials*, 2003, 6 (supp. 2), p. 44.

Wokulski, Z., "On the Microstructure of As-Grown Tin Whisker-Like Crystals," *Phys. Stat. Sol.*, 2001, pp. 251-260, vol. 183, No. 2.

Robbie, K. and Brett, M.J., "Sculptured Thin Films and Glancing Angle Deposition: Growth Mechanics and Applications," *J. Vac. Sci. Technol.*, May/Jun. 1997, pp. 1460-1465, vol. 15, No. 3.

Nolan, T.A., Allard, L.F., Coffey, D.W., Hubbard, C.R., & Padgett, R.A., "Microstructure and Crystallography of Titanium Nitride Whiskers Grown by a Vapor-Liquid-Solid Process," *J. Am. Ceram. Soc.*, 1991, pp. 2769-2775, vol. 74, No. 11.

Wagner, R.S. & Ellis, W.C., "Vapor-Liquid-Solid Mechanism of Single Crystal Growth," *Applied Physics Letters*, Mar. 1, 1964, pp. 89-90, vol. 4, No. 5.

Nieto, M.M. & Russell, A.M., "Growth of Whiskers Due to Solid-To-Solid Phase Transformation in Zirconium," *J. Applied Physics*, 1964, p. 461, vol. 35.

Russell, A.M. & Abbott, R.C., "Whisker Growth From Iodide Titanium Wire," *J. Applied Physics*, 1958, p. 1130, vol. 29.

Kim, H.W., Kim, N.H., Myung, J.H., & Shim, S.H., "Characteristics of $Sno_2$ Fishbone-Like Nanostructures Prepared by the Thermal Evaporation," *Phys. Stat. Sol.*, 2005, pp. 1758-1772, vol. 202, No. 9.

Wang, S., Xia, G., He, H., Yi, K., Shao, J. & Fan, Z., "Structural and Optical Properties of Nanostructured $Tio_2$ Thin Films Fabricated by Glancing Angle Deposition," *J. Alloys and Compounds*, 2007, pp. 1287-1291, vol. 431.

\* cited by examiner

SPINULOSE TITANIUM NANOPARTICULATE SURFACES

BACKGROUND OF THE INVENTION

1. Field of the Invention

The invention relates generally to substrate surfaces modified with vapor plasma deposited titanium nanoparticulates, which under certain deposition conditions can form spinulous surfaces. The nanostructured coatings are effective scaffolds for cell adhesion.

2. Description of Background Art

Metals have long been recognized as capable of growing tiny hairs, often called whiskers, under certain conditions. The mechanism causing such growth is not well understood, but is frequently observed under conditions of mechanical or thermal stress as well as under conditions peculiar to electroplating processes. In digital circuits at high frequencies, such whiskers are able to act like mini antennae, causing circuit impedance. It is well documented that whiskers are found in zinc, silver, tin, zirconium and gold filaments used in a variety of applications. Whiskers have been observed to grow from metal films and coatings over a period of time.

Whiskers are generally found as hair-like nanostructure projections with relatively high aspect ratios. While cross sections are generally polygonal, some cross sections are reported to vary as hexagonal, diamond or circular projections (US patent application publication No. 2007/0018139). Thermal evaporation of tin powders on titanium nitride coated substrates can result in tin oxide fishbone-like nanostructures (Kim, et al., 2005).

Whiskers can be deliberately "grown" via several processes; including manipulation of temperature and/or pressure. TiN whiskers can be synthesized by reacting ammonium chloride, titanium, titania in the presence of a meta/carbon catalyst under nitrogen at appropriately high temperatures, as described in U.S. Pat. No. 5,665,326. Wokulski (2001) employed a chemical vapor deposition process to prepare TiN whiskers from a titanium chloride, nitrogen and hydrogen gas mixture. Similarly there are many other reports of synthesis of compound whiskers; for example, transition metal carbides (U.S. Pat. No. 4,756,971).

Depending on the metal, whisker growth may occur at room temperature for low melting metals such as tin. Other metals such as aluminum (Al) and titanium (Ti) generally exhibit whiskers at much higher temperatures. Suzuki, et al. (2006), for example, studied the growth of Al whiskers from pure Al after deposition on a surface oxidized silicon substrate in an electron beam evaporation apparatus at high temperature. Russell, et al. (1958) reported growth of titanium whiskers from titanium wire thermally cycled in vacuum from about 800-1100° C.

It is possible that metal crystal growth and subsequent whisker formation is promoted by various impurities or other elements in the metal.

Compositions employing titanium whiskers as strengthening materials in thermoplastic compositions for orthopedic applications, such as interjoint and disc gap filling have been described in U.S. Pat. Application No. 2004/0228898.

Several studies over the past several years have focused on the growth and nature of nanostructured thin films, with a special interest in control of physical vapor deposition. Metal oxides deposited at glancing angles result in controllable columnar microstructures depending on substrate motion variation (Robbie and Brett 1997). The glancing angle technique (GLAD), produces vapor deposited thin film microstructures with distinct helical columnar appearance (U.S. Pat. No. 6,248,422; U.S. Pat. No. 6,206,065).

Nanostructured surfaces of GLAD films have been suggested as having possible applications in chiral optics and, due to magnetic anisotropy, in development of information storage devices because of the ability to deposit materials such as silicon in the form of nanostructured helical columns. Hawkeye and Brett (2007) reviewed GLAD films and foresee applications in solar energy conversion, fuel cells, gas sensors, catalysts and electrochemical capacitors.

GLAD films produced from electron beam heated silicon deposited on glass were studied McIntosh, et al. (2003) to assess hTert fibroblast morphology and survival on the columnar surfaces created from silicon deposited over a range of angles. Adhesion, spreading and survival beyond one day were observed only on surfaces deposited at a 70° angle, despite the identical composition of the columns deposited at other angles.

SUMMARY OF THE INVENTION

The present invention relates to highly nanostructured metal surfaces and to a modified plasma vapor deposition method for reproducible production of such surfaces. Nanotextured spinulose titanium surfaces have been produced by controlled nanoplasma deposition (NPD) on a wide range of substrate surfaces. Cells, including osteoblasts, fibroblasts and endothelial cells strongly adhere to the nanostructured films formed during the deposition process.

There are several aspects of the invention that distinguish it from currently used methods for depositing metals on substrates to form nanostructured surfaces. The majority of reported deposition methods are physical vapor deposition procedures, often termed vapor-liquid-solid (or vapor-solid), chemical vapor deposition (CVD) processes or electron beam evaporation. The method of the present invention is also based on vapor deposition, using a plasma arc deposition procedure where low voltage, (<100 V), high current, (>5 A), discharge ablates a metal cathode in an evacuated chamber and an inert atmosphere so that the metal is deposited onto a substrate surface. Unexpectedly, unique nanostructural surface features can be obtained when metal vapor deposition is periodically cycled by reducing inert gas flow and plasma discharge for selected intervals, as discussed in further detail in the examples.

The novel spinulose surface of nano plasma deposited Ti exhibits features significantly different in appearance from previously reported vapor deposited metals and metal compounds. The nano-roughness appears during the deposition process as spikes on round particulates when the deposition is cycled under certain controlled conditions.

While the invention is illustrated with deposition of Ti on several commonly used substrates, the novel spinulose Ti coatings, as well as other nanostructured metal films, can be obtained as films without the supporting substrate. Ti, for example, may be deposited on a carbon substrate and the resulting film, such as the spinulose Ti film described herein can be isolated by burning off the carbon. Other readily removable or degradable substrates can be envisioned, which can be easily removed without altering the integrity of the film by dissolving a salt or similar dissolvable substrate.

Substrates suitable as temporary matrices for film deposition include various salts. Sodium or potassium chloride, for example, can be readily dissolved after NPD deposition of Ti or other metals. The particulate surface remaining after dissolution can be recovered as a film or powdered or used as a high surface area catalyst in bioreactors or in a number of other applications based on the unique nanostructure. As drug delivery vehicles, spinulose and other nanostructured particles with low surface energy can act as a reservoir for chemicals or biomolecules. The salt matrix is slowly dissolved, and can be used to release an attached drug in a time dependent manner.

The deposition method of the invention is a modified ion plasma deposition process in which a plasma is generated from metal target and deposited onto a substrate in a controlled atmosphere environment under reduced pressure. The metal plasma deposits as nanoparticulates, which after further deposition under the described controlled deposition cycling conditions will form unusual nanostructured surfaces. The nano plasma deposition process (NPD) is basically a vacuum deposition of ionized material generated as a plasma by applying voltage and current to a cathode target such that ionized particles are deposited on a substrate. Unique surface features of the deposited metals are formed under vacuum and/or in an inert atmosphere, typically an inert gas such as argon. The presence of oxygen or nitrogen may result in formation of metal oxides or nitrides, resulting in surface features different from the nanostructures formed from deposition of substantially pure metals.

The nanostructural features of metals deposited by the described NPD method are different from ion plasma deposited films where deposition is conducted for selected times, at different voltages or by varying the other deposition parameters. Serendipitously, it was found that a cycling or intermittent deposition from metal targets produced unexpected surface features on some of the deposited metal films. While nanostructuring was observed with cobalt, copper, nickel, hafnium, 316L stainless steel, nitanol, titanium 6-4, and silver, only pure titanium and aluminum of the metals tested formed distinctly different nanostructured surfaces. Particularly unique surface features were observed with titanium, which can be structured as a "spikey" surface when titanium deposition is conducted under a particular set of conditions.

The spinulose titanium nanostructured surfaces produced under defined NPD deposition conditions are obtained with commercially pure titanium (grade 2) and are not observed with other Ti compositions or alloys such as nitinol under similar deposition conditions. Using the described cycling deposition method, spinulose-type surfaces are not observed with aluminum, cobalt, copper, nickel, hafnium, 316L stainless steel, nitinol, silver or titanium 6-4 deposited from metal targets on stainless steel substrates. On the other hand, in some cases, these metals formed other types of unusual nanostructured surfaces which are distinctly different from the spinulose appearance of deposited titanium. Generally, with the exception of aluminum, the nickel, cobalt, copper, silver, hafnium, 316L stainless steel, nitinol and titanium 6-4 nanostructured surfaces are basically globular or stacked globular in shape. Aluminum was distinctly different from Ti and the other metals cyclically deposited NPD metals.

Pure aluminum metal deposited under the same conditions described for Ti has a stacked appearance with a geometric cube-like structure different from the structures observed with Ti and other metals. While spinulose surfaces for aluminum and other metals are not observed under the conditions used to produce spinulose Ti nanostructured surfaces, it may be possible to generate spinules by using modifications of the disclosed deposition procedures, such as, but not necessarily limited to, longer intervals between deposition cycles, distance from target and chamber pressure.

Accordingly, the method for producing spinulose titanium surfaces and the globular type surface features observed with other metals, except aluminum, is based on a plasma deposition method comprising generation of a plasma from a metal cathode. Distance of the deposition target from the substrate can affect the nanostructural features of the deposited metal and can be adjusted to the particular apparatus configurations and deposition conditions. The substrate is housed in a vacuum chamber and, while the base pressure does not appear critical for spinulose Ti formation, the selected pressure may influence how close the substrate should be to the target.

The deposition is preferably conducted under an inert gas, e.g., argon, atmosphere in order to avoid any chemical reaction with the metal being deposited. Titanium will react with some gases; for example, when nitrogen is present in the system, TiN may form. The deposited TiN is not spinulous; rather, as reported by others, the nanosurface typically has projections that are more whisker-like or column-like in appearance. In the disclosed method, an argon atmosphere is employed, care being taken to use gas of high purity so that trace components do not react with the ionized titanium produced in the plasma.

Spinulose nanostructured Ti surfaces can be formed as coatings or films on virtually any metal, plastic or ceramic surface, including stainless steel, titanium, CoCrMo, nitinol, glass or silicon, as well as on silicone, poly(methylmethacrylate) (PMMA), polyurethane (PU), polyvinyl chloride (PVC), polyethylene terephthalate glycol (PETG), polyetheretherketone (PEEK), polytetrafluoroethylene (PTFE), polyethylene terephthalate (PET), ultra high molecular weight polyethylene (UHMWPE), and polypropylene (PP). Other metals, including aluminum, gold, platinum and silver are also suitable substrates.

Deposition is performed using a periodic deposition or cycling process. Gas flow and plasma discharge into the vacuum chamber are allowed to progress for a specified period of time. Gas flow and plasma discharge are then reduced to near zero or completely stopped for a defined period of time before the cycle is reinitiated. This is an unusual step and appears to be important in obtaining the observed Ti spirulite structures. Images of the initially deposited Ti show that the metal ion plasma first deposits as substantially round nanoparticles. With additional cycling, the particulates develop a more spike-like structure with increasing surface coverage as the number of cycles is increased.

In the examples shown, and using a small-scale apparatus, about 3-9 cycles were typically run with about 5-15 min of deposition followed by about 5-90 min of "resting" when gas flow and plasma generation were significantly reduced or stopped completely. In the examples presented, distinct Ti spinulites were not observed until after about 3 cycles. More than 9 cycles generally increase the number and density of Ti spinulites, which can increase available surface area for attachment of biomolecules and/or drugs as well as increase coverage of substrate surface up to 85% or greater.

The morphology of the NPD coatings depends on the angle between the cathode surface normal and the direction of the substrate ($\theta_c$) and also the angle between the depositing flux and the substrate surface normal ($\theta_s$). Generally the most pronounced spinulose morphology can be produced with $\theta_c=90°$. As $\theta_s$ is decreased from 80° the structure of the spinulose coating grows more anisotropic. At oblique incidence angles the spinules tend to grow such that they point away from the depositing flux. This is opposite to the direction observed in GLAD (glancing angle deposition) reported by others (U.S. Pat. No. 6,248,422). Spinulose Ti surfaces are obtained from depositions with a flux $\theta_c=0°$ and $\theta_s$ ranging from 0° to 80° and with a flux $\theta_s=0°$ and $\theta_c$ ranging from 0° to 80°.

DEFINITIONS

Spinules, as used herein, and as defined in the American Heritage dictionary, are small spines, which are thorn-like in character. Alternatively known as "spinulites", particles having such a spiney appearance are characterized as "spinulose" as defined in Random House Unabridged Dictionary. Spinules are distinguished in appearance from larger, more hair-like appendages commonly characterized as whiskers or columnar structures and which are typically wire or rod-like in appearance.

Whiskers are hair-like projections typically seen on the surface of many metals and metal alloys. Thermopolymers have been imbedded with metal whiskers in order to improve material strength. Similar structures have also been deliberately grown from crystals in order to study crystal structures or incorporated as nanostructured monolithic materials into ceramics.

As used herein, "substantially" is intended to indicate a limited range of up to 10% of any value indicated.

As used within the context of the claimed subject matter, the term "a" is not intended to be limited to a single material or element.

Physical vapor deposition (PVD) is used to describe a class of processes that involve the deposition of material, often in the form of a thin film, from a condensable vapor which has been produced from a solid precursor by physical means. There are many ways of producing the vapor, and many modifications to each of these processes. Examples of PVD processes include evaporation, sputtering, laser ablation and arc discharge. PVD can involve chemical reactions, such as from multiple sources, or by addition of a reactive gas.

Chemical vapor deposition (CVD) is the growth of material from a gas phase precursor, due to reaction or reactions that often occur on a surface. The reactions are frequently promoted by using an elevated substrate temperature. Alternatively the reactions can be achieved by enhancing the reactivity of the precursors using a plasma (PECVD) or hot wire.

Atomic Layer Deposition is a CVD method involving growing materials by pulsing multiple precursors that react with a surface in a self-limiting manner.

Electron beam evaporation is use of an electron beam to heat a metal so that it evaporates. The vapor can be deposited on a surface.

Biomolecules are agents or materials that have some biological interactions; e.g., drugs, proteins, cells and bioorganisms such as bacteria and viruses.

DETAILED DESCRIPTION OF THE INVENTION

The present invention provides metal nanostructured surfaces by controlling plasma deposition conditions. In a particular embodiment, spinulose titanium nanostructured surfaces are described, which have strong adhesion for several cell types, including osteoblasts, fibroblasts and endothelial cells. Most metals are initially deposited as relatively round plasma-deposited particles. Titanium also initially deposits as round nanoparticulates but after several cycles forms spine-like or spinulous projections. Most other metals continue to deposit as globular structures with increased deposition times. Titanium spinules are relatively uniform and can be grown from plasmas deposited in a range of angles with θs and θc ranging from 0° to 80°.

Most vacuum based methods for preparing thin films or depositing materials on surfaces are physical vapor deposition or chemical vapor deposition methods. These methods differ from electrodeposition wet chemistry methods. The nanostructured surfaces of the present invention are produced by a modified cyclic plasma arc deposition procedure termed nano plasma deposition (NPD). The apparatus for producing the ion plasmas is shown in FIG. 1.

NPD deposited particles are typically round and may be varied in size and distribution by changing power and/or time of deposition. Under certain specified deposition conditions, titanium metal particles develop nanosized spike-like protrusions, which are observed as spinules or small thorny spines. The spinules are distinct in character and appearance from the tiny filiform hairs commonly termed "whiskers", which have been reported as crystalline metallurgical phenomena commonly found associated with metal components in electrical equipment and computer machinery and which can lead to system malfunctions and failures. Titanium spinules only form under certain deposition conditions and are distinctly different from such whiskers and from the glancing angle structures (GLAD) reported by others.

Figure 1:
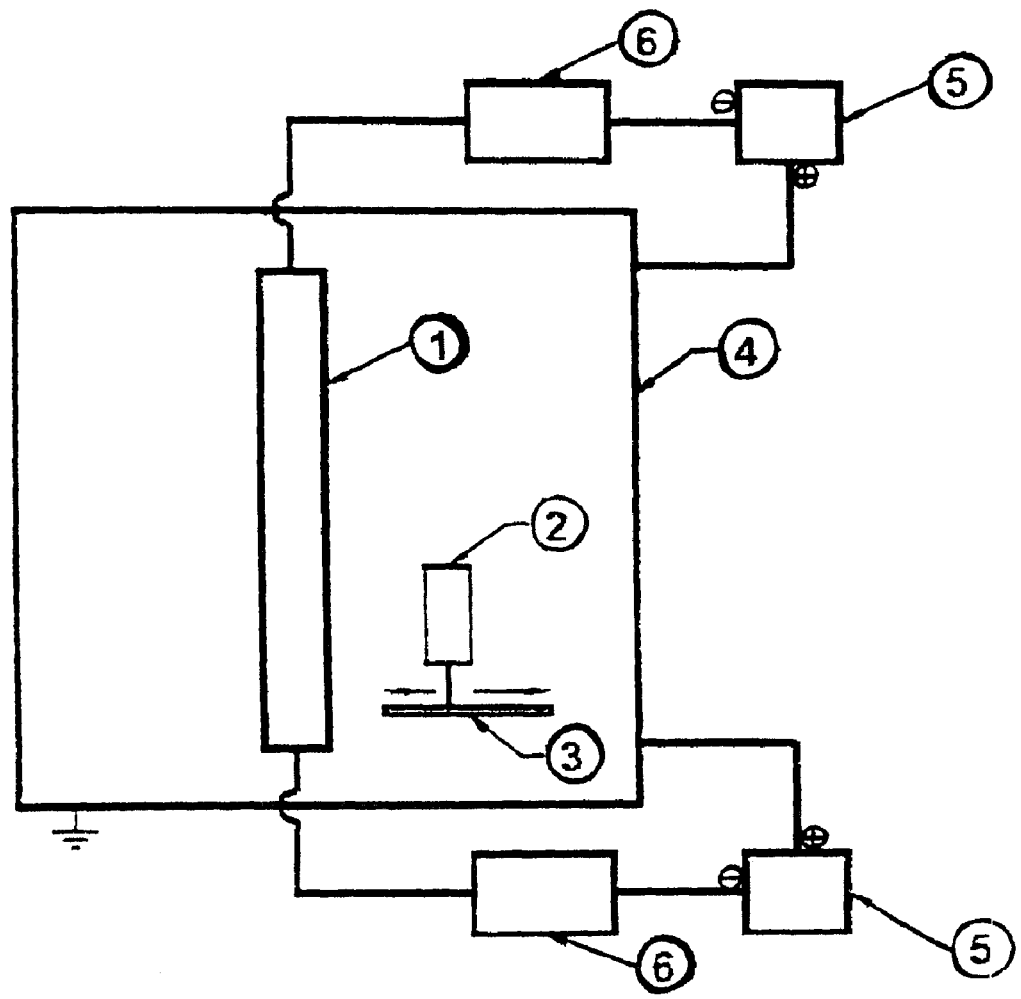
FIG. 1 is a sketch of a typical ion plasma deposition apparatus; pure metal cathode target 1; substrate 2; substrate holder 3; vacuum chamber 4; power supply for target 5; and are control 6. Not shown is an inlet into the vacuum chamber 4 for introducing an inert gas flow.

Metal cathode targets are disposed in a vacuum chamber as illustrated in FIG. 1. An inert gas, typically argon, is introduced into the evacuated chamber and deposition commenced. The substrate 2 is generally positioned 8-28 in from the target and deposition is conducted intermittently for periods of approximately 1-15 min. During the intervals between depositions, there is no plasma discharge and the inert gas flow can be reduced to zero or stopped completely if desired. The intervals between depositions can be varied and are about 5-90 min with a typical run of about 3-9 cycles.

Figure 3:
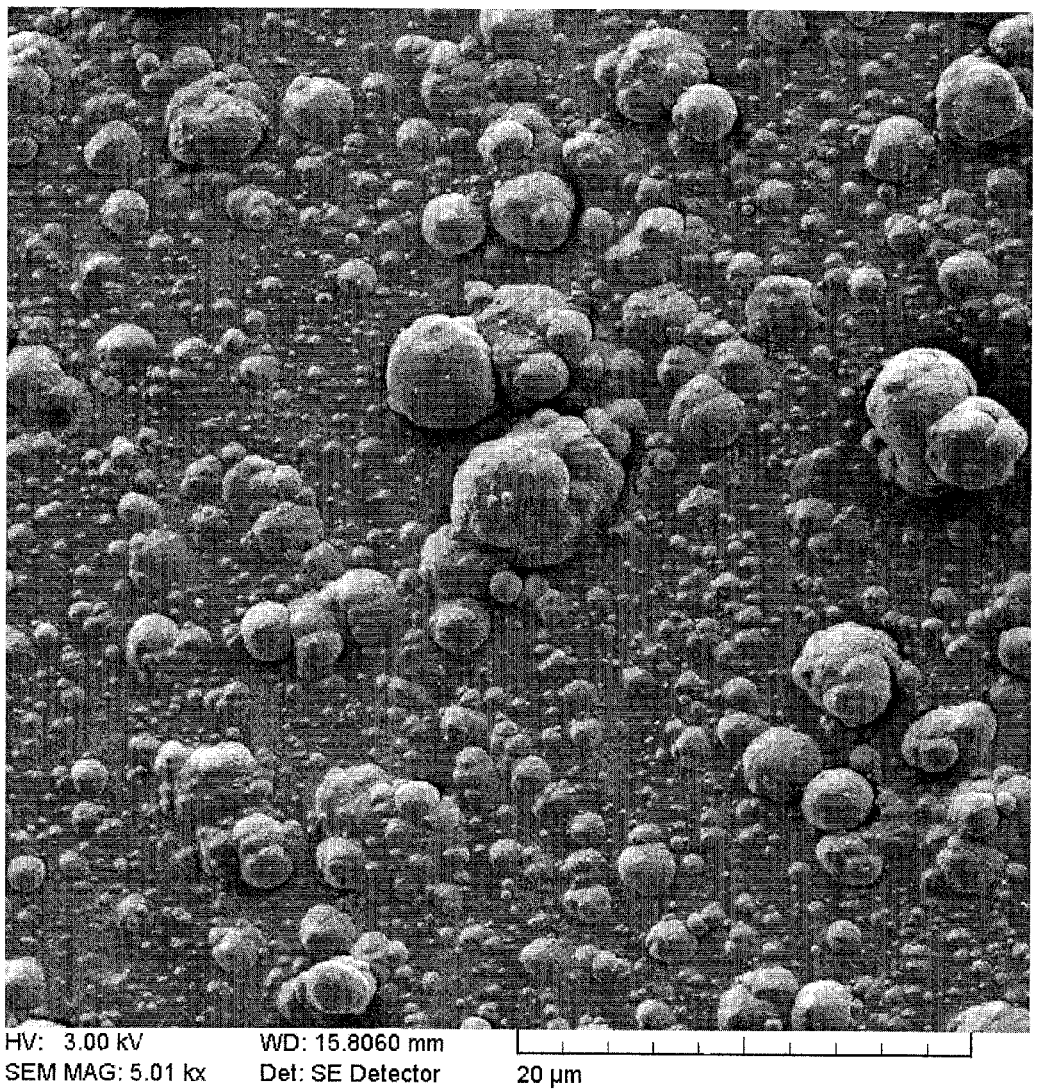
FIG. 3 is a FEG-SEM image of a titanium round coating formed from a titanium plasma deposited at an angle of $\theta_c=0°$ with a θs of 0° on 316L stainless steel.

Titanium spinulose nanostructured surfaces appear to be relatively uniform, with the spiky projections ranging in lengths of about 0.166-1.119 μm and widths of about 0.156-0.627 μm depending on number of deposition cycles and distance from the target. The number of cycles can be increased; however with a fewer number of cycles, generally less than 3, as shown in FIG. 3, no spinules are observed. Increasing cycles above three results in the emergence of spikey protrusions on some of the deposited round particles, while increasing to 9 or more cycles greatly increases the density of spinulose particles.

Using similar cycling parameters, aluminum was deposited in what appears to be geometric polygonal structures including some cube-like attachments on surfaces of round particles. Spinulose surfaces were not observed.

Copper, cobalt, silver, nitinol, titanium 6-4, 316L stainless steel, and hafnium also form nanostructured films when deposited under the described cycling conditions. These metals differ in structural detail from NPD deposited titanium and aluminum and are more similar to each other in having a globular appearance. Nickel, in contrast to the other metals has a more random and "rough" appearance.

Titanium spinulose nanostructures are also formed when the angle of deposition, θs, from the target is varied. The spinules are oriented away from the plasma flow and appear to be more prominent around the circumference of the round particles on which they form as the angle is changed.

Figure 4:
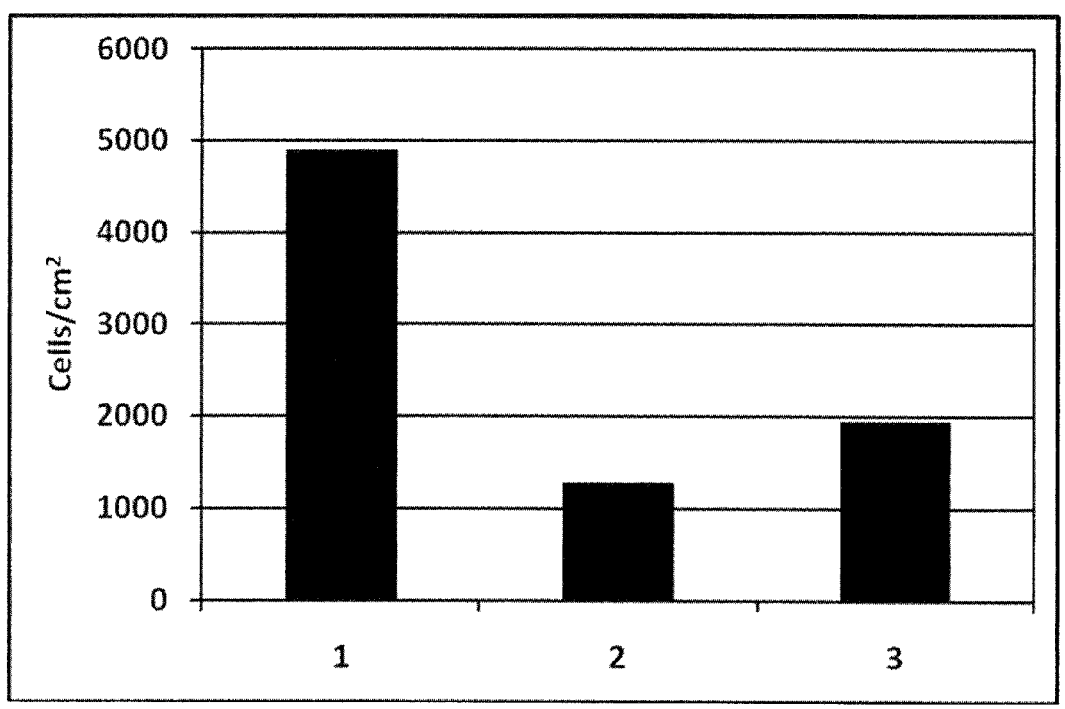
FIG. 4 compares human osteoblast cell adhesion on 316L stainless steel coated with a spinulose coating formed from titanium deposited at an angle of $\theta_c=0°$ with a θs of 0° (1); no coating (2) and titanium round coating formed from a titanium plasma deposited at an angle of $\theta_c=0°$ with a θs of 0° (3).
Figure 5:
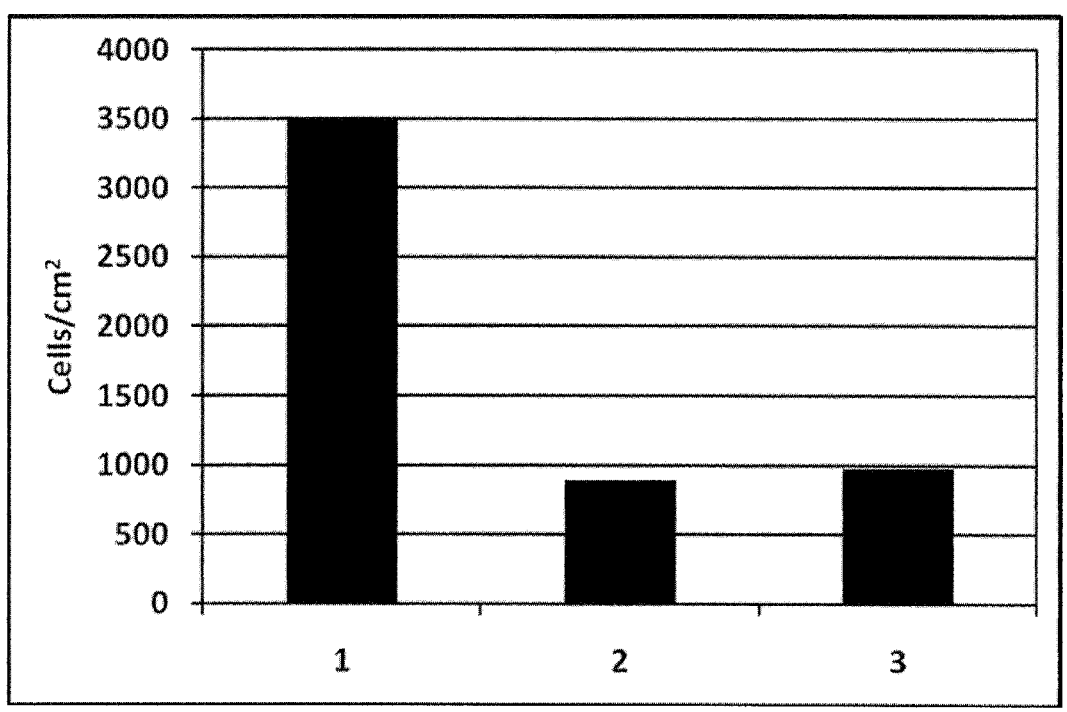
FIG. 5 compares human skin fibroblast cell adhesion on 316L stainless steel coated with a spinulose coating formed from titanium deposited at an angle of $\theta_c=0°$ with a θs of 0° (1); no coating (2) and titanium round coating formed from a titanium plasma deposited at an angle of $\theta_c=0°$ with a θs of 0° (3).
Figure 6:
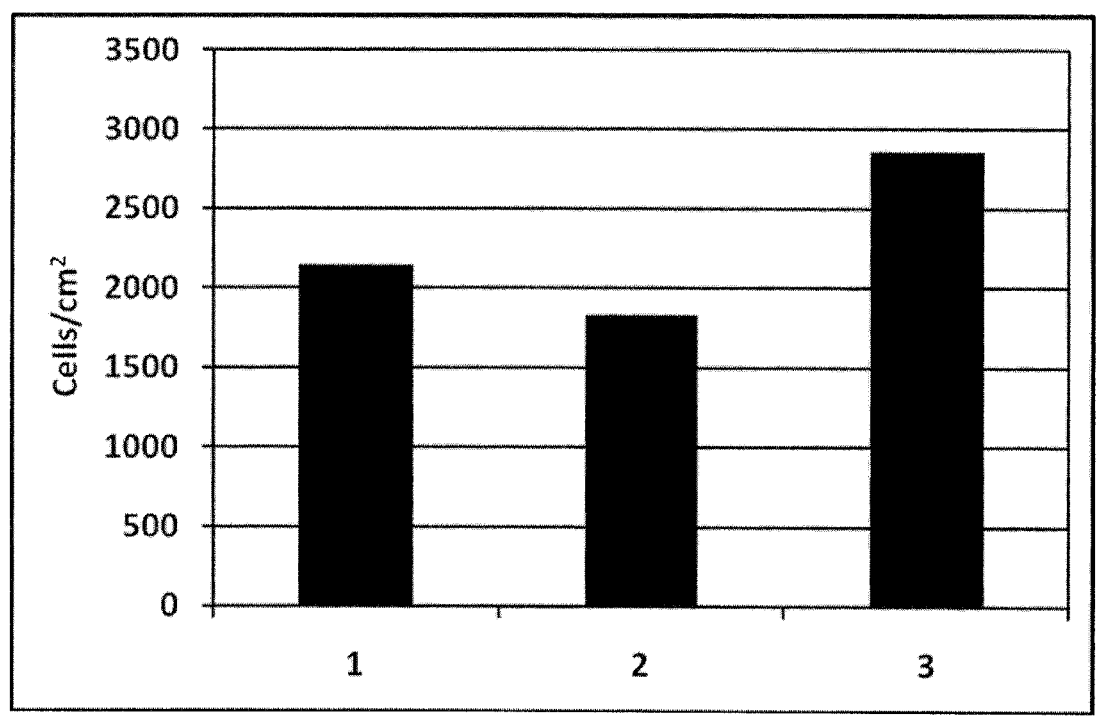
FIG. 6 compares human umbilical artery endothelial cell adhesion on stainless steel coated with a spinulose coating formed from titanium deposited at an angle of $\theta_c=0°$ with a θs of 0° (1); no coating (2) and titanium round coating formed from a titanium plasma deposited at an angle of $\theta_c=0°$ with a θs of 0° (3).

Titanium spinulose surfaces are excellent scaffolds for osteoblast and fibroblast cell attachment. As shown in FIG. 4 and FIG. 5, titanium spinulose surfaces were superior compared to uncoated surfaces and to surfaces lacking the spinulite structural nanofeatures. FIG. 6 indicates that endothelial cells attached better to Ti spinulose surfaces than to uncoated surfaces but were less effective than Ti nanostructured surfaces lacking the spinulose features.

Figure 10:
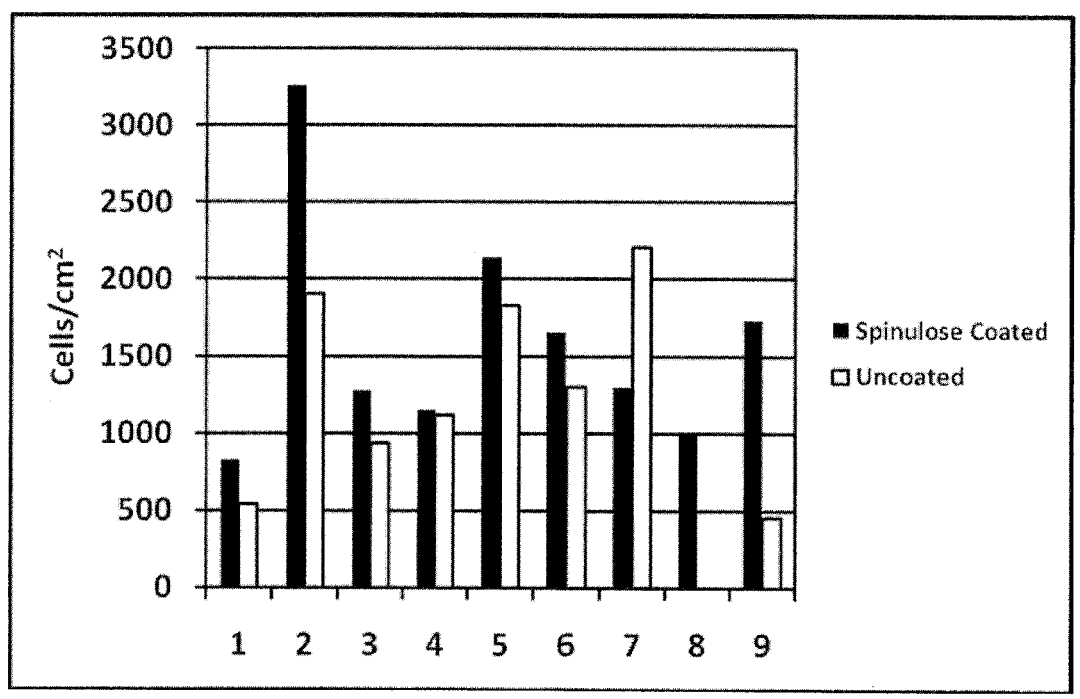
FIG. 10 shows human umbilical artery endothelial cell adhesion on UHMWPE (1); PTFE (2); PVC (3); PET (4); 316L stainless steel (5); silicone (6); titanium (7); PU (8) and PMMA 9 coated with titanium spinulose coating formed from a titanium plasma deposited at an angle of $\theta_c=0°$ with a θs of 0° compared to the respective uncoated substrate.

Cell adhesion is better on all deposited spinulose Ti substrates with the exception of endothelial cells on a Ti spinulose coated titanium substrate, see FIG. 10.

Figure 19:
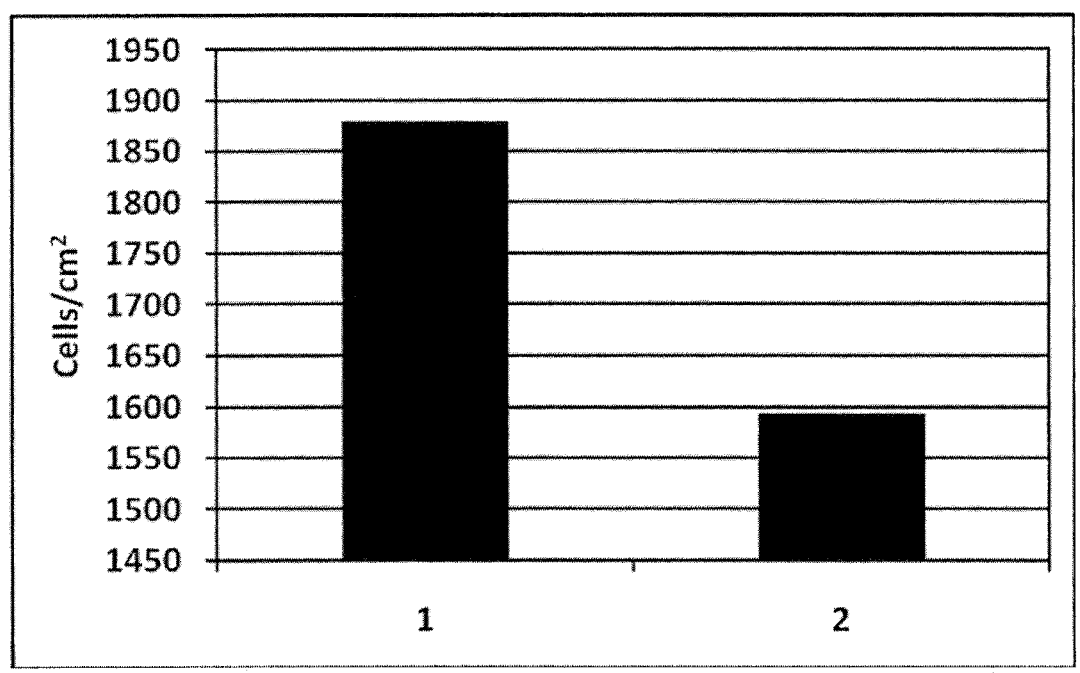
FIG. 19 shows human osteoblast cell adhesion on 316L stainless steel coated with an aluminum geometric coating formed from an aluminum plasma deposited at an angle of θc=0° with a θs of 0° (1) compared to the respective uncoated substrate (2).
Figure 20:
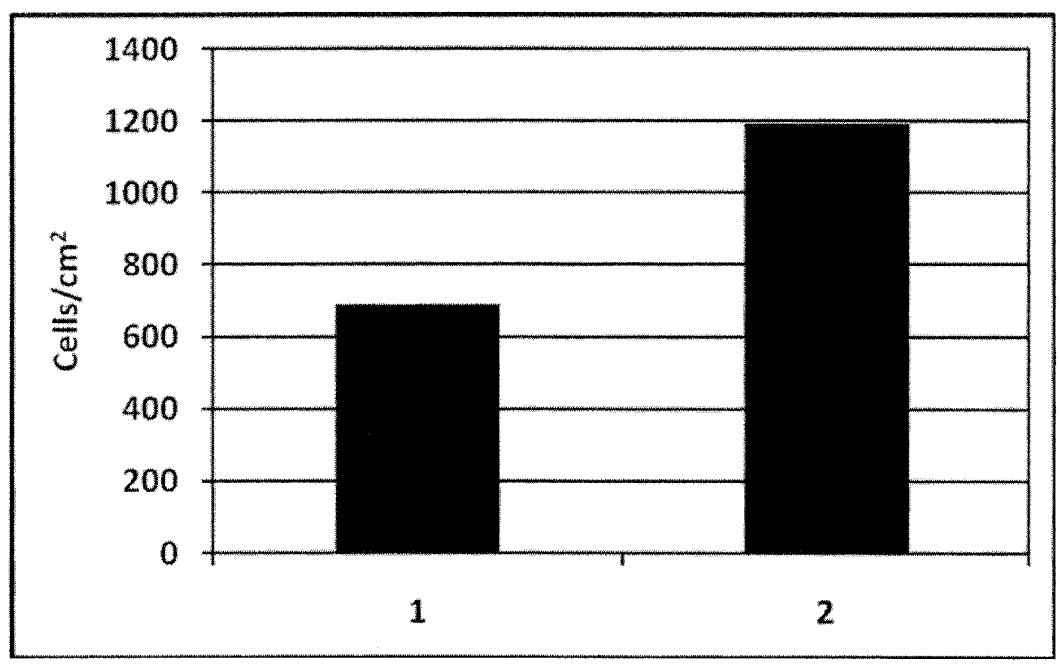
FIG. 20 shows human skin fibroblast cell adhesion on 316L stainless steel coated with an aluminum geometric coating formed from an aluminum plasma deposited at an angle of θc=0° with a θs of 0° (1) compared to the respective uncoated substrate (2).
Figure 21:
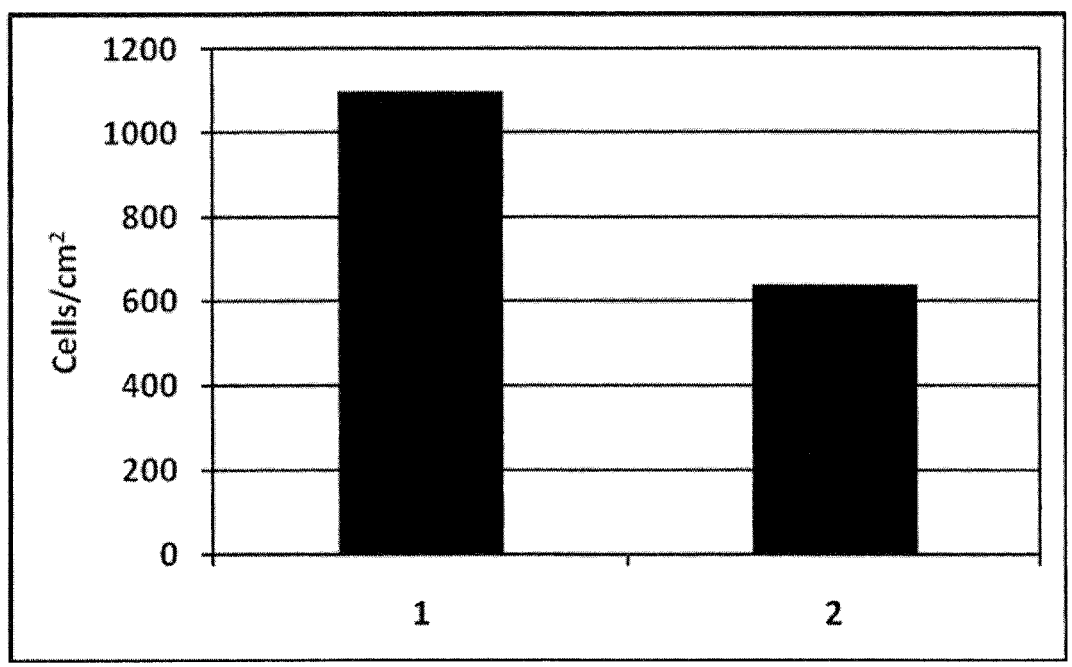
FIG. 21 shows human umbilical artery endothelial cell adhesion on 316L stainless steel coated with an aluminum geometric coating formed from an aluminum plasma deposited at an angle of θc=0° with a θs of 0° (1) compared to the respective uncoated substrate (2).

The unique aluminum coatings deposited by the described cycling NPD deposition method show good cell adhesion for osteoblasts and endothelial cells, FIG. 19 and FIG. 21, but not for fibroblast adhesion, FIG. 20.

EXAMPLES

The following examples are provided as illustrations of the invention and are in no way to be considered limiting.

Materials and Methods

Human Osteoblast cells (CRL-11372) were purchased from American Type Culture Collection (Rockville, Md.) as frozen cultures in complete media: 1:1 Ham's F12 medium and Dulbecco's modified Eagle's medium without phenol red with 2.5 mM L-glutamine, 10% FBS and 0.3 μg/ml G418.

Briefly, the vials were thawed, centrifuged and the cells resuspended in complete media before transfer into a culture device and incubated at 34° C. in 5% carbon dioxide. The cells were then subcultured in complete media after treating with trypsin-EDTA at either 34° C. or 39° C. Doubling time was 36 hr at 33.5° C. and 96 hr at 38.0° C. If not used immediately, the cells were stored frozen in complete media with DMSO added to each vial.

Human fibroblast cells (CRL-1502) were purchased from American Type Culture Collection as frozen cultures in complete media containing Eagle's minimal essential medium with Earle's BSS and 2 mM L-glutamine (EMEM) modified to contain 1.0 mM sodium pyruvate, 0.1 M non-essential amino acids, 1.5 g/L sodium bicarbonate supplemented with 10% FBS and 10 U/mL penicillin/streptomycin.

Human endothelial cells were purchased from VEC Technologies (Rensselaer, N.Y.) as frozen cultures in MCDB-131 media.

Cell sample vials were thawed at 37° C., centrifuged and the cell pellet resuspended in complete media before transfer to a culture device and incubated at 34° C. in 5% carbon dioxide.

Cells were subcultured by rinsing and adding trypsin-EDTA before culturing in complete media and incubating at 34° C. or 39° C. If not used immediately, the cells were rinsed and stored in liquid nitrogen after addition of 10% FBS and DMSO to the vials.

Example 1

Nanoplasma Deposition of Titanium

Substrates used were stainless steel, nitinol, CoCrMo alloy, silicon, titanium, glass, silicone, poly(methyl methacrylate) PMMA, polyurethane (PU), polytetrafluoroethylene (PTFE), polyvinyl chloride) (PVC), polyethylene terephthalate (PET), ultra high molecular weight polyethylene (UHMWPE), polyethylene terephthalate glucol (PETG), polyetheretherketone (PEEK) and polypropylene (PP). Samples were prepared with an approximate surface area of 1 cm$^2$. Except for the silicon which was delivered clean, all the other substrate materials were ultrasonically cleaned before deposition in detergent (ChemCrest #275 at 160° F.), rinsed in deionized water and dried in hot air.

Clean substrates were then placed in the chamber and exposed to nano-plasma deposition (NPD). The cathode was commercially pure titanium cathode (grade 2). The substrates were mounted in the vacuum chamber at distances from 8 to 28 in from the cathode (measured from the centre of the cathode). The angle between the cathode surface normal and a line from the centre of the cathode to the substrate, θc, was varied in the range 0-80°. The angle between the depositing flux and the substrate surface normal, θs, was varied in the range of 0-80°.

The angle between the substrate surface normal and a line from the centre of the cathode to the substrate, θc, was varied in the range of 0-80°. The angle between the depositing flux and the substrate surface, θs, was varied in the range of 0-80°. The chamber was pumped to a base pressure of between 1.33 mPa and 0.080 mPa. The arc current was varied from a 150 A to 300 A with an argon flow of 0 to 300 standard cubic centimeter per minute (sccm).

The process was run in cycles, with each cycle consisting of plasma discharge intervals (varied over the range 1 to 15 minutes) followed by intervals where there was no discharge and no gas flow (between 5 and 810 minutes). Each process consisted of 3-9 cycles.

Following plasma deposition, the samples were characterized by scanning electron microscopy (SEM), and cell adhesion tests with osteoblasts, fibroblasts and endothelial cells.

SEM images were obtained with a Tescan Mira Field Emission instrument (Pittsburgh, Pa.) equipped with a SE detector, at a magnification of 50.00K and 10.00K times at 10.00 kV.

Experiments were carried out with a range of different conditions, substrates and tests. Results are shown in Tables 1-3.

Table 1 lists the properties of spinulose titanium deposited on silicon or stainless steel substrates. All examples were run with an argon gas flow of 100 sccm, deposited for 5 min with a 90 min interval between depositions through 9 cycles. The substrates were positioned 13 in from the cathode. θc was 0° for all substrates.

TABLE 1

| Substrate | Current (A) | θs (°) | SPSC[1] (%) | RPSC[2] (%) | ASBW[3] (μm) | ASH[4] (μm) |
|---|---|---|---|---|---|---|
| SS | 200 | 45 | 98 | 2 | 0.362 | 0.616 |
| SS | 300 | 55 | 98 | 2 | 0.426 | 0.777 |
| Si | 300 | 55 | 98 | 2 | 0.627 | 1.119 |
| SS | 300 | 70 | 98 | 2 | 0.435 | 0.696 |
| Si | 300 | 70 | 98 | 2 | 0.413 | 0.723 |
| SS | 300 | 50 | 98 | 2 | 0.394 | 0.657 |
| Si | 300 | 50 | 98 | 2 | 0.361 | 0.653 |
| SS | 300 | 80 | 98 | 2 | 0.346 | 0.662 |
| Si | 300 | 80 | 98 | 2 | 0.364 | 1.068 |
| SS | 300 | 0 | 98 | 2 | 0.298 | 0.914 |
| Si | 300 | 0 | 85 | 5 | 0.377 | 0.567 |

[1]Spinulose Particle Surface Coverage
[2]Round Particle Surface Coverage
[3]Average Spike Base Width
[4]Average Spike Height Table 2 shows the effect of alterations in rest interval, distance from cathode, number of cycles and θc for cyclic depositions of titanium on silicon and stainless steel substrates. For these examples, the arc current was 200 A, the argon gas flow 100 SCCM and θs was 0° for all substrates

TABLE 2

| Substrate | Run (min) | Rest Interval (min) | No. cycles | Distance from cathode (in) | Θc (°) | SPSC[1] (%) | RPSC[2] (%) | ASBW[3] (μm) | ASH[4] (μm) |
|---|---|---|---|---|---|---|---|---|---|
| SS | 5 | 90 | 9 | 8 | 0 | 70 | 5 | 0.316 | 0.720 |
| Si | 5 | 90 | 9 | 8 | 0 | 20 | 10 | 0.223 | 0.420 |
| SS | 5 | 90 | 9 | 13 | 0 | 88 | 2 | 0.409 | 0.798 |
| Si | 5 | 90 | 9 | 13 | 0 | 68 | 2 | 0.435 | 0.954 |
| SS | 5 | 90 | 9 | 8 | 5 | 53 | 2 | 0.284 | 0.700 |
| Si | 5 | 90 | 9 | 8 | 5 | 60 | 10 | 0.401 | 0.770 |
| SS | 5 | 90 | 9 | 13 | 5 | 55 | 5 | 0.287 | 0.538 |
| Si | 5 | 90 | 9 | 13 | 5 | 45 | 10 | 0.267 | 0.412 |
| SS | 5 | 90 | 9 | 8 | 10 | 45 | 5 | 0.290 | 0.450 |
| Si | 5 | 90 | 9 | 8 | 10 | 40 | 15 | 0.243 | 0.454 |
| SS | 5 | 90 | 9 | 13 | 10 | 68 | 2 | 0.293 | 0.455 |
| Si | 5 | 90 | 9 | 13 | 10 | 40 | 5 | 0.373 | 0.891 |
| SS | 5 | 90 | 9 | 8 | 15 | 35 | 5 | 0.268 | 0.501 |
| Si | 5 | 90 | 9 | 8 | 15 | 25 | 15 | 0.267 | 0.399 |
| SS | 5 | 90 | 9 | 13 | 15 | 80 | 5 | 0.308 | 0.618 |

TABLE 2-continued

| Substrate | Run (min) | Rest Interval (min) | No. cycles | Distance from cathode (in) | Θc (°) | SPSC[1] (%) | RPSC[2] (%) | ASBW[3] (μm) | ASH[4] (μm) |
|---|---|---|---|---|---|---|---|---|---|
| Si | 5 | 90 | 9 | 13 | 15 | 50 | 10 | 0.310 | 0.584 |
| Si | 5 | 90 | 9 | 13 | 20 | 48 | 2 | 0.352 | 0.853 |
| Si | 5 | 90 | 9 | 13 | 25 | 40 | 50 | 0.288 | 0.254 |
| SS | 5 | 90 | 9 | 13 | 30 | 75 | 5 | 0.277 | 0.379 |
| SS | 5 | 90 | 9 | 13 | 40 | 75 | 5 | 0.262 | 0.383 |
| SS | 5 | 90 | 9 | 13 | 50 | 70 | 10 | 0.249 | 0.354 |
| SS | 5 | 90 | 9 | 13 | 60 | 70 | 10 | 0.257 | 0.223 |
| SS | 5 | 90 | 9 | 10 | 70 | 65 | 20 | 0.195 | 0.263 |
| SS | 5 | 90 | 9 | 8 | 80 | 65 | 20 | 0.208 | 0.242 |
| SS | 5 | 30 | 9 | 13 | 0 | 88 | 2 | 0.447 | 1.000 |
| Si | 5 | 30 | 9 | 13 | 0 | 58 | 2 | 0.388 | 1.048 |
| Si | 5 | 30 | 9 | 8 | 5 | 48 | 2 | 0.484 | 1.007 |
| SS | 5 | 30 | 9 | 13 | 5 | 70 | 5 | 0.387 | 1.077 |
| Si | 5 | 30 | 9 | 13 | 5 | 18 | 2 | 0.319 | 0.706 |
| Si | 5 | 30 | 9 | 8 | 10 | 10 | 30 | 0.307 | 0.546 |
| SS | 5 | 30 | 9 | 13 | 10 | 60 | 5 | 0.414 | 1.085 |
| Si | 5 | 30 | 9 | 13 | 10 | 45 | 5 | 0.374 | 0.907 |
| SS | 5 | 30 | 9 | 13 | 15 | 60 | 5 | 0.320 | 0.640 |
| Si | 5 | 30 | 9 | 13 | 15 | 10 | 25 | 0.390 | 0.615 |
| SS | 5 | 30 | 9 | 13 | 20 | 40 | 5 | 0.336 | 0.559 |
| Si | 5 | 30 | 9 | 13 | 20 | 10 | 25 | 0.345 | 0.452 |
| Si | 5 | 30 | 9 | 13 | 25 | 55 | 5 | 0.301 | 0.866 |
| SS | 5 | 30 | 3 | 8 | 0 | 65 | 5 | 0.302 | 0.816 |
| Si | 5 | 30 | 3 | 8 | 0 | 43 | 2 | 0.34 | 0.861 |
| SS | 5 | 30 | 3 | 13 | 0 | 68 | 2 | 0.278 | 0.807 |
| Si | 5 | 30 | 3 | 13 | 0 | 38 | 2 | 0.272 | 0.887 |
| SS | 5 | 30 | 3 | 8 | 5 | 30 | 5 | 0.369 | 0.744 |
| Si | 5 | 30 | 3 | 8 | 5 | 45 | 5 | 0.379 | 0.862 |
| SS | 5 | 30 | 3 | 13 | 5 | 35 | 5 | 0.236 | 0.430 |
| Si | 5 | 30 | 3 | 13 | 5 | 30 | 5 | 0.259 | 0.873 |
| SS | 5 | 30 | 3 | 8 | 10 | 35 | 5 | 0.268 | 0.493 |
| Si | 5 | 30 | 3 | 8 | 10 | 25 | 5 | 0.364 | 0.652 |
| SS | 5 | 30 | 3 | 13 | 10 | 28 | 2 | 0.225 | 0.583 |
| Si | 5 | 30 | 3 | 13 | 10 | 15 | 5 | 0.268 | 0.782 |
| SS | 5 | 30 | 3 | 8 | 10 | 15 | 5 | 0.304 | 0.492 |
| Si | 5 | 30 | 3 | 8 | 15 | 5 | 25 | 0.238 | 0.367 |
| SS | 5 | 30 | 3 | 13 | 15 | 35 | 5 | 0.244 | 0.527 |
| Si | 5 | 30 | 3 | 13 | 15 | 18 | 2 | 0.280 | 0.752 |
| Si | 5 | 30 | 3 | 13 | 20 | 30 | 5 | 0.305 | 0.836 |
| Si | 5 | 30 | 3 | 13 | 25 | 30 | 5 | 0.265 | 0.803 |

[1]Spinulose Particle Surface Coverage
[2]Round Particle Surface Coverage
[3]Average Spike Base Width
[4]Average Spike Height Table 3 shows the properties of spinulose titanium surfaces on several different substrates with θs and θc equal to 0°.

TABLE 3

| Substrate | Run (min) | Rest Interval (min) | No. cycles | Current (A) | Gas Flow (SCCM) | Distance (in) | SPSC[1] (%) | RPSC[2] (%) | ASBW[3] | ASH[4] |
|---|---|---|---|---|---|---|---|---|---|---|
| SS | 5 | 90 | 9 | 200 | 100 | 3.5 | | | | |
| SS | 5 | 90 | 9 | 200 | 100 | 10.5 | 70 | 10 | 0.214 | 0.481 |
| SS | 5 | 90 | 9 | 200 | 100 | 12 | 93 | 2 | 0.297 | 0.554 |
| SS | 5 | 90 | 9 | 200 | 100 | 15.5 | 60 | 2 | 0.257 | 0.342 |
| SS | 5 | 90 | 9 | 200 | 100 | 25 | 60 | 2 | 0.216 | 0.372 |
| SS | 5 | 90 | 9 | 200 | 100 | 28 | 35 | 5 | 0.176 | 0.287 |
| Ti | 5 | 90 | 9 | 200 | 100 | 13 | 98 | 2 | 0.358 | 0.710 |
| Anodized Ti | 5 | 90 | 9 | 200 | 100 | 13 | 85 | 2 | 0.328 | 0.880 |
| NiTiNol | 5 | 90 | 9 | 200 | 100 | 13 | 98 | 2 | 0.317 | 0.654 |
| CoCrMo | 5 | 90 | 9 | 200 | 100 | 13 | 95 | 2 | 0.326 | 0.616 |
| Si | 5 | 90 | 9 | 200 | 100 | 13 | 88 | 2 | 0.256 | 0.703 |
| PET | 5 | 90 | 9 | 200 | 100 | 13 | 75 | 5 | 0.367 | 0.680 |
| PTFE | 5 | 90 | 9 | 200 | 100 | 13 | 70 | 5 | 0.357 | 0.640 |
| PVC | 5 | 90 | 9 | 200 | 100 | 13 | 70 | 5 | 0.308 | 0.620 |
| PU | 5 | 90 | 9 | 200 | 100 | 13 | 70 | 5 | 0.267 | 0.505 |
| S | 5 | 90 | 9 | 200 | 100 | 13 | 80 | 5 | 0.244 | 0.613 |
| PETG | 5 | 90 | 9 | 200 | 100 | 13 | 98 | 8 | 0.309 | 0.669 |

TABLE 3-continued

| Substrate | Run (min) | Rest Interval (min) | No. cycles | Current (A) | Gas Flow (SCCM) | Distance (in) | SPSC[1] (%) | RPSC[2] (%) | ASBW[3] | ASH[4] |
|---|---|---|---|---|---|---|---|---|---|---|
| PP | 5 | 90 | 9 | 200 | 100 | 13 | 80 | 2 | 0.387 | 0.860 |
| PMMA | 5 | 90 | 9 | 200 | 100 | 13 | 85 | 2 | 0.287 | 0.542 |
| UHMWPE | 5 | 90 | 9 | 200 | 100 | 13 | 95 | 2 | 0.260 | 0.542 |
| PEEK | 5 | 90 | 9 | 200 | 100 | 13 | 78 | 2 | 0.279 | 0.658 |
| Glass | 5 | 90 | 9 | 200 | 100 | 13 | 88 | 2 | 0.471 | 0.913 |
| S | 5 | 90 | 9 | 200 | 150 | 13 | 80 | 5 | 0.288 | 0.528 |
| SS | 5 | 90 | 9 | 200 | 150 | 13 | 93 | 2 | 0.347 | 0.811 |
| SS | 5 | 90 | 9 | 200 | 300 | 13 | 85 | 5 | 0.329 | 0.727 |
| CoCrMo | 5 | 90 | 9 | 200 | 300 | 13 | 85 | 5 | 0.333 | 0.545 |
| PET | 5 | 90 | 9 | 200 | 300 | 13 | 85 | 10 | 0.357 | 0.583 |
| PTFE | 5 | 90 | 9 | 200 | 300 | 13 | 98 | 2 | 0.303 | 0.585 |
| PVC | 5 | 90 | 9 | 200 | 300 | 13 | 98 | 2 | 0.350 | 0.688 |
| PU | 5 | 90 | 9 | 200 | 300 | 13 | 85 | 5 | 0.342 | 0.383 |
| S | 5 | 90 | 9 | 200 | 300 | 13 | 85 | 5 | 0.286 | 0.510 |
| PMMA | 5 | 90 | 9 | 200 | 300 | 13 | 85 | 10 | 0.333 | 0.546 |
| UHMWPE | 5 | 90 | 9 | 200 | 300 | 13 | 85 | 10 | 0.279 | 0.578 |
| SS | 5 | 90 | 9 | 300 | 100 | 13 | 98 | 2 | 0.298 | 0.914 |
| Ti | 5 | 90 | 9 | 300 | 100 | 13 | 50 | 20 | 0.343 | 0.436 |
| Si | 5 | 90 | 9 | 300 | 100 | 13 | 85 | 5 | 0.377 | 0.567 |
| SS | 5 | 60 | 9 | 150 | 200 | 13 | 60 | 5 | 0.299 | 0.595 |
| Ti | 5 | 60 | 9 | 150 | 200 | 13 | 90 | 5 | 0.272 | 0.589 |
| NiTiNol | 5 | 60 | 9 | 150 | 200 | 13 | 70 | 5 | 0.226 | 0.444 |
| CoCrMo | 5 | 60 | 9 | 150 | 200 | 13 | 70 | 5 | 0.238 | 0.478 |
| Si | 5 | 60 | 9 | 150 | 200 | 13 | 60 | 5 | 0.265 | 0.704 |
| PET | 5 | 60 | 9 | 150 | 200 | 13 | 60 | 5 | 0.229 | 0.584 |
| PTFE | 5 | 60 | 9 | 150 | 200 | 13 | 30 | 5 | 0.242 | 0.531 |
| PVC | 5 | 60 | 9 | 150 | 200 | 13 | 75 | 2 | 0.267 | 0.488 |
| PU | 5 | 60 | 9 | 150 | 200 | 13 | 55 | 10 | 0.264 | 0.470 |
| S | 5 | 60 | 9 | 150 | 200 | 13 | 45 | 5 | 0.298 | 0.456 |
| PETG | 5 | 60 | 9 | 150 | 200 | 13 | 75 | 5 | 0.313 | 0.822 |
| PP | 5 | 60 | 9 | 150 | 200 | 13 | 60 | 5 | 0.295 | 0.738 |
| PMMA | 5 | 60 | 9 | 150 | 200 | 13 | 80 | 2 | 0.283 | 0.485 |
| UHMWPE | 5 | 60 | 9 | 150 | 200 | 13 | 80 | 5 | 0.251 | 0.553 |
| PEEK | 5 | 60 | 9 | 150 | 200 | 13 | 30 | 10 | 0.308 | 0.731 |
| SS | 5 | 30 | 9 | 200 | 100 | 13 | 88 | 2 | 0.447 | 1.000 |
| Si | 5 | 30 | 9 | 200 | 100 | 13 | 58 | 2 | 0.388 | 1.048 |
| SS | 5 | 5 | 9 | 150 | 100 | 8 | 93 | 2 | 0.425 | 0.853 |
| Si | 5 | 5 | 9 | 150 | 100 | 8 | 55 | 5 | 0.340 | 0.502 |
| SS | 5 | 5 | 9 | 150 | 100 | 13 | 30 | 5 | 0.273 | 0.414 |
| Si | 5 | 5 | 9 | 150 | 100 | 13 | 25 | 5 | 0.328 | 0.726 |
| SS | 5 | 5 | 9 | 150 | 100 | 19 | 30 | 5 | 0.325 | 0.366 |
| Si | 5 | 5 | 9 | 150 | 100 | 19 | 30 | 5 | 0.264 | 0.548 |
| SS | 1 | 18 | 9 | 200 | 100 | 13 | 35 | 5 | 0.275 | 0.482 |
| CoCrMo | 1 | 18 | 9 | 200 | 100 | 13 | 35 | 5 | 0.240 | 0.419 |
| Ti | 1 | 18 | 9 | 200 | 100 | 13 | 35 | 5 | 0.266 | 0.437 |
| SS | 1 | 9 | 9 | 200 | 100 | 13 | 38 | 2 | 0.269 | 0.453 |
| CoCrMo | 1 | 9 | 9 | 200 | 100 | 13 | 43 | 2 | 0.229 | 0.453 |
| Ti | 1 | 9 | 9 | 200 | 100 | 13 | 38 | 2 | 0.256 | 0.440 |
| SS | 15 | 5 | 3 | 150 | 100 | 8 | 78 | 2 | 0.307 | 0.401 |
| Si | 15 | 5 | 3 | 150 | 100 | 8 | 45 | 5 | 0.219 | 0.342 |
| SS | 15 | 5 | 3 | 150 | 100 | 13 | 30 | 10 | 0.319 | 0.523 |
| Si | 15 | 5 | 3 | 150 | 100 | 13 | 35 | 5 | 0.233 | 0.365 |
| SS | 15 | 5 | 3 | 150 | 100 | 19 | 5 | 15 | 0.267 | 0.393 |
| Si | 15 | 5 | 3 | 150 | 100 | 19 | 15 | 5 | 0.272 | 0.393 |
| Si | 5 | 60 | 3 | 200 | 0 | 13 | 20 | 10 | 0.247 | 0.412 |
| SS | 5 | 30 | 3 | 150 | 100 | 8 | 45 | 5 | 0.381 | 0.825 |
| Si | 5 | 30 | 3 | 150 | 100 | 8 | 35 | 5 | 0.300 | 0.663 |
| SS | 5 | 30 | 3 | 150 | 100 | 13 | 40 | 5 | 0.267 | 0.830 |
| Si | 5 | 30 | 3 | 150 | 100 | 13 | 18 | 2 | 0.239 | 0.923 |
| SS | 5 | 30 | 3 | 150 | 100 | 19 | 13 | 2 | 0.218 | 0.559 |
| Si | 5 | 30 | 3 | 150 | 100 | 19 | 13 | 2 | 0.214 | 0.489 |
| SS | 5 | 30 | 3 | 200 | 100 | 8 | 65 | 5 | 0.302 | 0.816 |
| Si | 5 | 30 | 3 | 200 | 100 | 8 | 43 | 2 | 0.340 | 0.861 |
| SS | 5 | 30 | 3 | 200 | 100 | 13 | 68 | 2 | 0.278 | 0.807 |
| Si | 5 | 30 | 3 | 200 | 100 | 13 | 38 | 2 | 0.272 | 0.887 |
| PTFE | 5 | 30 | 3 | 200 | 100 | 13 | 45 | 5 | 0.289 | 0.269 |
| PVC | 5 | 30 | 3 | 200 | 100 | 13 | 40 | 10 | 0.270 | 0.218 |
| PET | 5 | 30 | 3 | 200 | 100 | 13 | 30 | 5 | 0.260 | 0.323 |
| SS | 5 | 30 | 3 | 200 | 100 | 19 | 18 | 2 | 0.252 | 0.700 |
| Si | 5 | 30 | 3 | 200 | 100 | 19 | 23 | 2 | 0.208 | 0.670 |
| SS | 5 | 5 | 3 | 150 | 100 | 8 | 43 | 2 | 0.389 | 0.798 |
| Si | 5 | 5 | 3 | 150 | 100 | 8 | 48 | 2 | 0.461 | 0.965 |
| SS | 5 | 5 | 3 | 150 | 100 | 13 | 15 | 5 | 0.255 | 0.356 |
| Si | 5 | 5 | 3 | 150 | 100 | 13 | 28 | 2 | 0.364 | 0.840 |

TABLE 3-continued

| Substrate | Run (min) | Rest Interval (min) | No. cycles | Current (A) | Gas Flow (SCCM) | Distance (in) | SPSC[1] (%) | RPSC[2] (%) | ASBW[3] | ASH[4] |
|---|---|---|---|---|---|---|---|---|---|---|
| SS | 5 | 5 | 3 | 150 | 100 | 19 | 8 | 2 | 0.186 | 0.319 |
| Si | 5 | 5 | 3 | 150 | 100 | 19 | 8 | 2 | 0.207 | 0.258 |

[1]Spinulose Particle Surface Coverage
[2]Round Particle Surface Coverage
[3]Average Spike Base Width
[4]Average Spike Height Example 2

Spinulose Titanium Nanostructured Surfaces 316L stainless steel substrates (1.6 cm²×0.1 cm, mirror polished (McMaster-Carr, Elmhurst, Ill.) were cleaned in an ultrasonic bath, rinsed with deionized water and dried in air. The substrates were placed in the vacuum chamber on a floating holder approximately 13 in from the cathode surface at an angle of $\theta c=0°$ with a $\theta s$ of $0°$. Prior to deposition, the chamber was pumped to a base pressure of at least 0.088 mPa.

The deposition was carried out in 5 minute intervals with 90 min intervals of no arc current and no gas flow. This deposition-pause cycle was repeated 9 times. A 300 A arc discharge was generated in a background of 160 mPa of argon on a pure titanium (grade 2) cathode (20 in×6 in).

Samples were imaged in a FEG-SEM (Tescan Mira), operated with an accelerating voltage of 10 kV. The images showed a pronounced spinulose morphology (see FIG. 2) with the fraction of surface area covered by spinulose features estimated to be at least 85%.

A second batch of coated substrates was prepared as above except that deposition was conducted continuously for 45 min. The deposited titanium surface exhibited a rounded surface morphology quite distinct from the spinulose coatings observed using interval deposition, and is referred to here as "round" coating (see FIG. 3).

Human osteoblast, human skin fibroblast and human umbilical artery endothelial cell four hr adhesion tests were carried out on 316L stainless steel coated with a titanium spinulose coating formed from a titanium plasma deposited at an angle of $\theta c=0°$ with a $\theta s$ of $0°$ and compared with cell adhesion on respective substrates coated with titanium round coating formed from a titanium plasma deposited at an angle of $\theta c=0°$ with a $\theta s$ of $0°$ and with uncoated substrates. The substrates were placed in wells using sterilized tweezers and exposed to UV light for one hour. The substrates were then rinsed with 2.0 mL of room temperature (1×PBS). The desired amount of room temperature Complete Media (supplemented with FBS and antibiotic) was added to each well. The cells were seeded onto the substrates at 2500 cells/cm² and incubated at 34° C., 5% $CO_2$ for four hours. Following incubation, the media and non-adherent cells were removed. The substrates were then rinsed with room temperature 1×PBS and fixed with 4% paraformaldehyde. The nuclei of adherent cells were fluorescently stained with Hoescht stain and counted using a fluorescent microscope.

FIG. 4 and FIG. 5 compare the results of the human osteoblast and human skin fibroblast four hr cell adhesion tests on 316L stainless steel coated with a titanium spinulose coating from a titanium plasma deposited at an angle of $\theta c=0°$ with a $\theta s$ of $0°$ (1); no coating (2); and a titanium round coating from a titanium plasma deposited at an angle of $\theta c=0°$ with a $\theta s$ of $0°$ (3), respectively. There is an increase in the number of osteoblasts and the number of fibroblasts attached to the spinulose coated substrate compared to the uncoated and the round coated substrates.

FIG. 6 compares the results of the human umbilical artery endothelial four hr cell adhesion test on 316L stainless steel coated with a titanium spinulose coating formed from a titanium plasma deposited at an angle of $\theta c=0°$ with a $\theta s$ of $0°$ (1); no coating (2); and a titanium round coating from a titanium plasma deposited at an angle of $\theta c=0°$ with a $\theta s$ of $0°$ (3). The spinulous coated substrates show growth inhibition of endothelial cells compared to growth on the round coated substrates while simultaneously demonstrating an increase in adhesion compared to the uncoated substrates.

Example 4

Spinulose Titanium Coated Polymer Substrates

Titanium was deposited by nanoplasma deposition as in Example 2 on several different substrates. The following materials were used as substrates: PTFE, PET, PETG, PEEK, PMMA, PVC, PU, UHMWPE, PP and silicone.

PTFE, PET (1 cm²×0.5 cm) substrates (McMaster-Carr), silicone (1.3 cm²×0.3 cm) substrates (McMaster-Carr), PMMA, PVC, PU and UHMWPE (1.2 cm outer diameter× 1.3 cm length) cylindrical shaped substrates from McMaster-Carr) were cleaned in an ultrasonic bath, rinsed in deionized water and dried in air. The substrates were placed in the chamber on a floating holder approximately 13 in from the cathode surface at an angle of $\theta c=0°$ with a $\theta s$ of $0°$. Prior to deposition the chamber was pumped to a base pressure of at least 0.907 mPa.

The deposition was carried out in 5 minute intervals, with 90 minute pauses in between of no arc current and no gas flow. This deposition-pause cycle was repeated 9 times. A 200 A arc discharge was generated in a background of 440 mPa of argon on a pure titanium (grade 2) cathode (20 in by 6 in).

Figure 11:
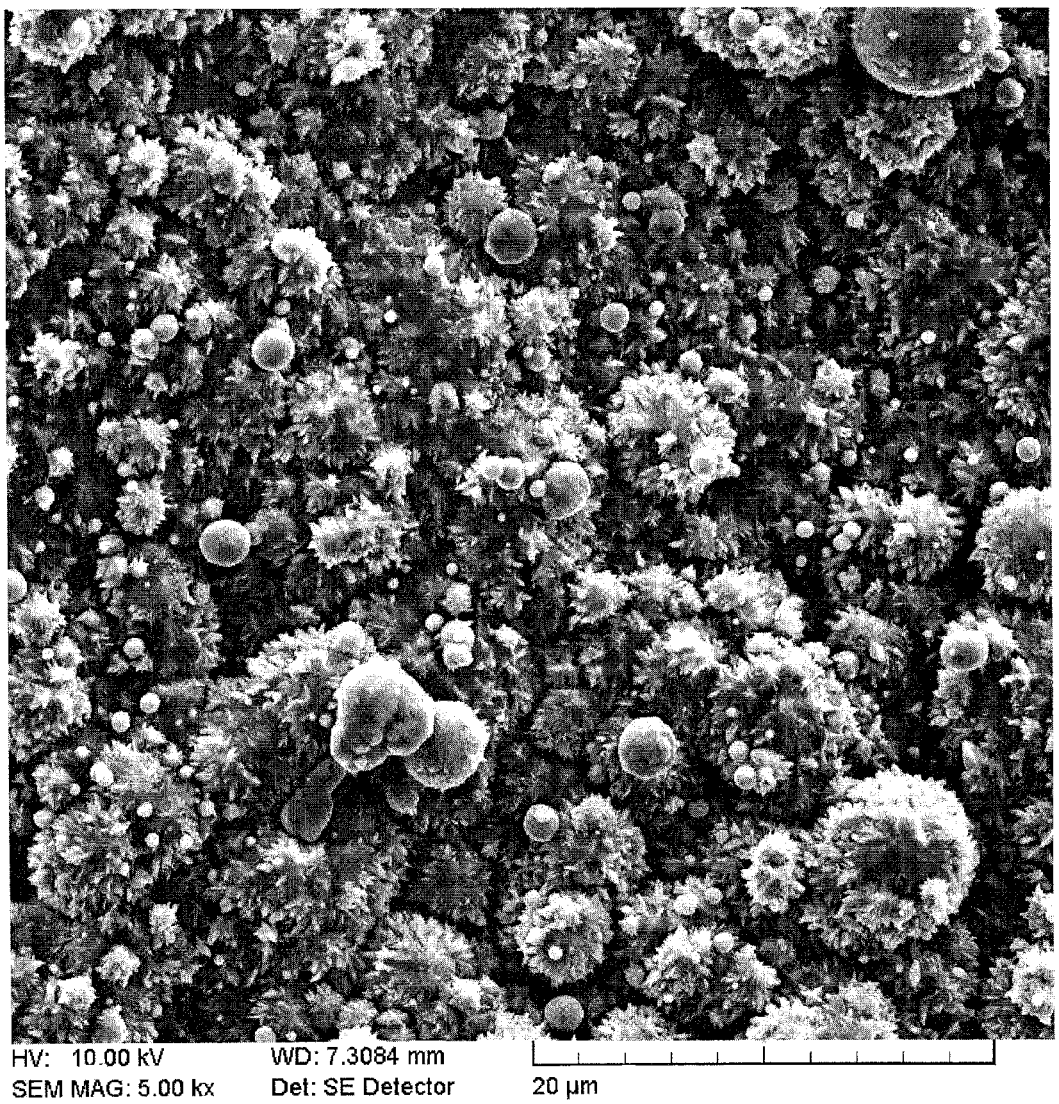
FIG. 11 is a FEG-SEM image of a titanium spinulose coating formed from a titanium plasma deposited an angle of $\theta_c=0°$ with a θs of 0° on PTFE.

Samples were imaged in a FEG-SEM (Tescan Mira), operated with an accelerating voltage of 10 kV. The images showed a pronounced spinulose morphology (see FIG. 11) with a fraction of surface area covered by spinulose features estimated to be at least 85%.

Human osteoblast, human skin fibroblast and human umbilical artery endothelial cell four hr adhesion tests were carried out on UHMWPE, PTFE, PVC, PET, silicone, PU and PMMA substrates coated with a titanium spinulose coating formed from a titanium plasma deposited at an angle of $\theta c=0°$ with a $\theta s$ of $0°$ and compared with cell adhesion on the respective uncoated substrates. Substrates were placed in wells using sterilized tweezers and exposed to UV light for one hour. Each substrate was then rinsed with 2.0 mL of room temperature (1×PBS). The desired amount of room temperature Complete Media (supplemented with FBS and antibiotic) was added to each well. The cells were seeded onto the substrates at 2500 cells/cm² and incubated at 34° C., 5% $CO_2$ for four hours. Following incubation, the media and non-adherent cells were removed. The substrates were then rinsed with room temperature (1×PBS) and fixed with 4% paraformaldehyde. The nuclei of adherent cells were fluorescently stained with Hoescht stain and counted using a fluorescent microscope.

Figure 8:
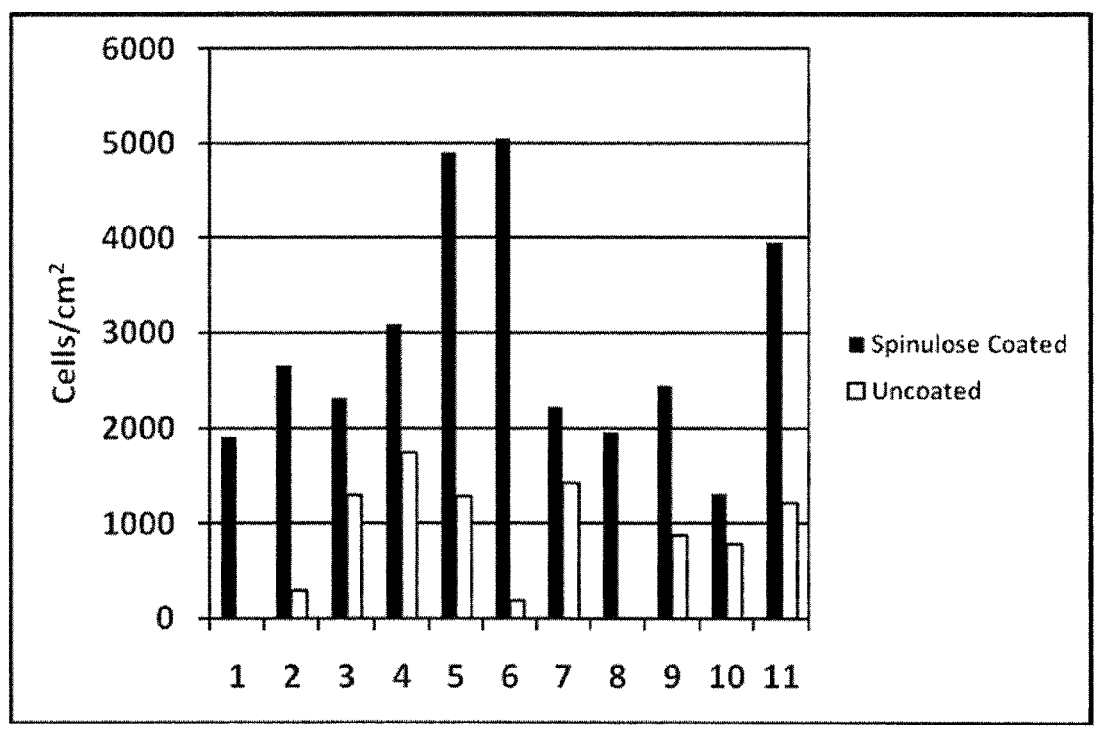
FIG. 8 shows human osteoblast cell adhesion on UHMWPE (1); PTFE (2); PVC (3); PET (4); 316L stainless steel (5); silicone (6); titanium (7); PU (8); PMMA (9); CoCrMo (10); and nitinol (11) coated with titanium spinulose coating formed from a titanium plasma deposited at an angle of $\theta_c=0°$ with a θs of 0° compared to the respective uncoated substrate.
Figure 9:
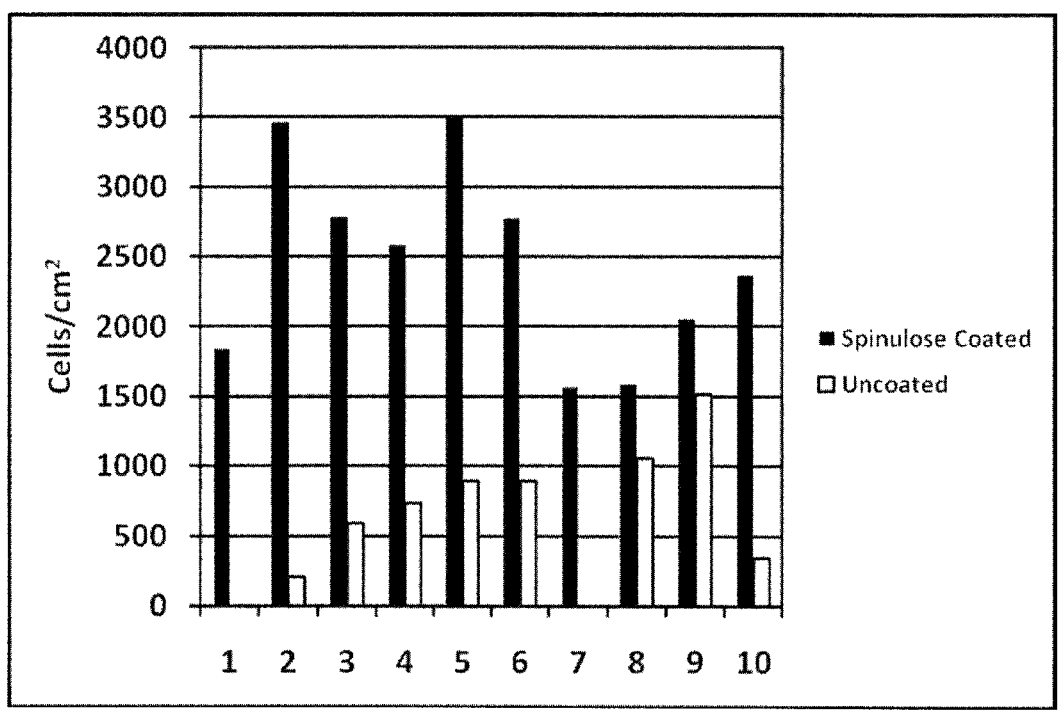
FIG. 9 shows human skin fibroblast cell adhesion on UHMWPE (1); PTFE (2); PVC (3); PET (4); 316L stainless steel (5); silicone (6); PU (7); PMMA (8); CoCrMo (9); and nitinol (10) coated with titanium spinulose coating formed from a titanium plasma deposited at an angle of $\theta_c=0°$ with a θs of 0° compared to the respective uncoated substrate.

FIGS. 8, 9 and 10 compare the results of the human osteoblast, human skin fibroblast and human umbilical artery endothelial cell four hour cell adhesion tests, respectively. FIG. 8 shows an increase in the number of human osteoblast cells that adhered to the surface of the UHMWPE, PTFE, PVC, PET, silicone, PU and PMMA substrates coated with a titanium spinulose coating formed from a titanium plasma deposited at an angle of θc=0° with a θs of 0° over that of the respective uncoated substrates. FIG. 9 shows an increase in the number of human skin fibroblast cells that adhered to the surface of UHMWPE, PTFE, PVC, PET, silicone, PU and PMMA substrates coated with a titanium spinulose coating formed from a titanium plasma deposited at an angle of θc=0° with a θs of 0° over that of the respective uncoated substrates. FIG. 10 shows an increase in the number of human umbilical artery endothelial cells that adhered to the surface of UHMWPE, PTFE, PVC, PET, silicone, PU and PMMA substrates coated with a titanium spinulose coating formed from a titanium plasma deposited at an angle of θc=0° with a θs of 0° over that of the respective uncoated substrates.

Example 3

Spinulose Titanium Coatings

Titanium was deposited by nanoplasma deposition as in Example 2 on several different substrates. The following materials were used as substrates: silicon, glass, anodized titanium, titanium, CoCrMo, and NiTiNol.

Silicon (1 cm² by 0.04 cm), single crystal (100) silicon wafers from (Encompass Distribution Services, LLC), glass (18 mm micro cover glass circles (VWR) and anodized titanium (1.25 cm² by 0.2 cm), wire cut substrates (Alfa Aesar) were cleaned by blowing compressed air over the surface of the substrates before placing in chamber. Titanium (1.6 cm² by 0.6 cm), shear cut substrates from McMaster-Carr), CoCrMo (1.8 cm (outer diameter)×1.3 cm (height), cylindrical shaped, machine cut stubs (Voss Metals Company, Inc.), Nitinol (1.2 cm (outer diameter) by 0.6 cm (length), cylindrical shaped, machine cut stubs from NiTiNol Devices and Components) were cleaned in an ultrasonic bath, rinsed in deionized water and dried in air. The substrates were placed in the chamber on a floating holder 13 in from the cathode surface at an angle of θc=0° with a θs of 0°. Prior to deposition, the chamber was pumped to a base pressure of at least 0.288 mPa.

The deposition was carried out in 5 minute intervals, with 90 minute intervals between deposition and no arc current and no gas flow. The deposition-pause cycle was repeated 9 times. A 200 A arc discharge was generated in a background of 160 mPa of argon on a pure titanium (grade 2) cathode (20 in×6 in).

Figure 7:
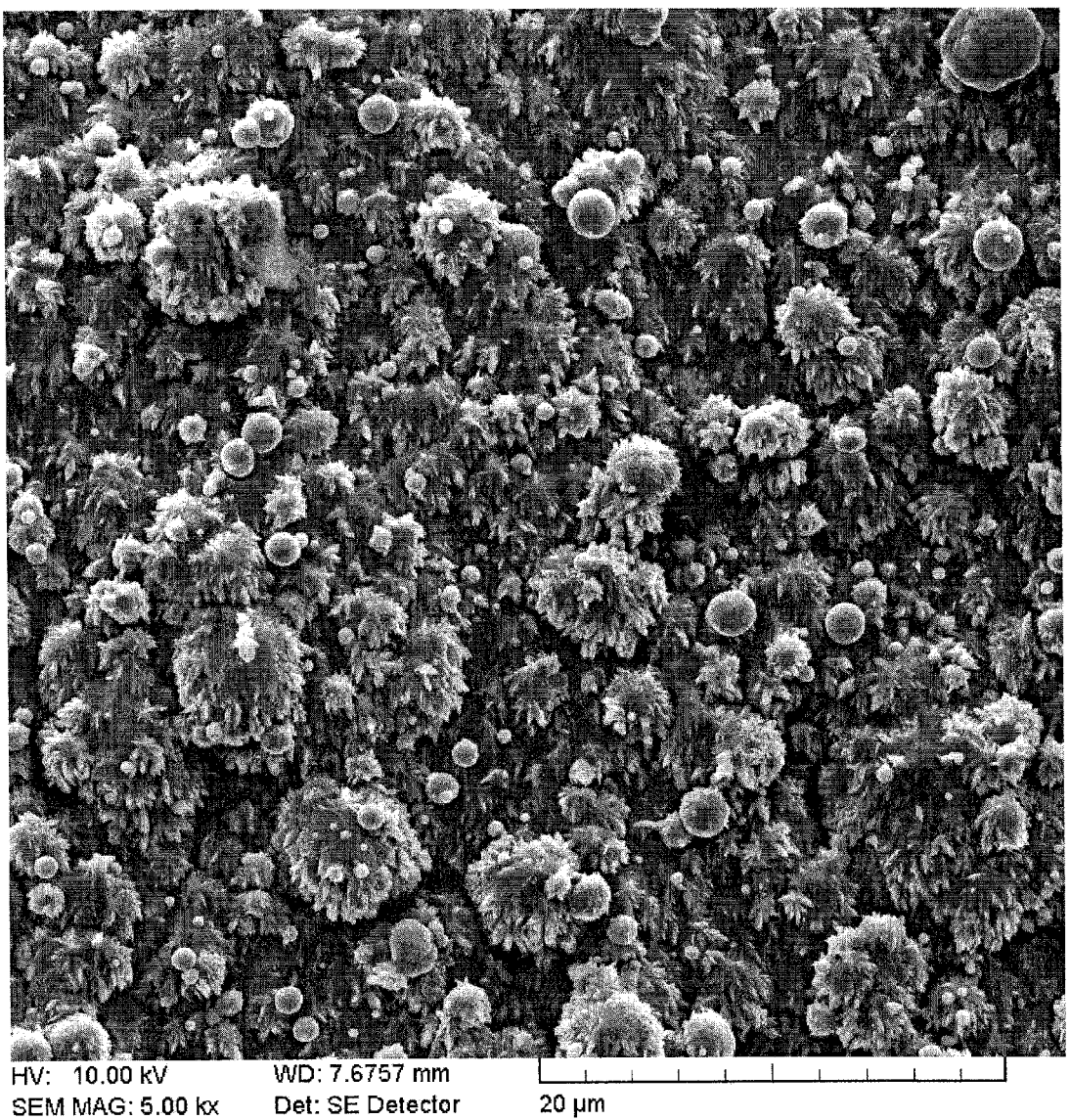
FIG. 7 is a FEG-SEM image of titanium spinulose coating formed from a titanium plasma deposited at an angle of $\theta_c=0°$ with a θs of 0° on nitinol.

Samples were imaged in a FEG-SEM (Tescan Mira), operated with an accelerating voltage of 10 kV. The images showed a pronounced spinulose morphology (see FIG. 7) with a fraction of surface area covered by spinulose features estimated to be at least 85%.

Human osteoblast, human skin fibroblast and human umbilical artery endothelial four hr cell adhesion tests were carried out on spinulose coated titanium, CoCrMo and nitinol substrates and compared with cell adhesion on the respective uncoated substrates. Substrates were placed in wells using sterilized tweezers and exposed to UV light for one hour. Each substrate was then rinsed with 2.0 mL of room temperature (1×PBS). The desired amount of room temperature Complete Media (supplemented with FBS and antibiotic) was added to each well. The cells were seeded onto the substrates at 2500 cells/cm² and incubated at 34° C., 5% $CO_2$ for four hrs. Following incubation, the media and non-adherent cells were removed. The substrates were then rinsed with room temperature (1×PBS) and fixed with 4% paraformaldehyde. The nuclei of adherent cells were fluorescently stained with Hoescht stain and counted using a fluorescent microscope.

FIGS. 8, 9 and 10 compare the results of the human osteoblast, human skin fibroblast and human umbilical artery endothelial four hour cell adhesion test, respectively. FIG. 8 shows an increase in the number of human osteoblast cells that adhered to the surface of the spinulose coated titanium, CoCrMo and NiTiNol substrates coated with a titanium spinulose coating formed from a titanium plasma deposited at an angle of θc=0° with a θs of 0° over that of the respective uncoated substrates. FIG. 9 shows an increase in the number of human skin fibroblast cells that adhered to the surface of CoCrMo and NiTiNol substrates coated with a titanium spinulose coating formed from a titanium plasma deposited at an angle of θc=0° with a θs of 0° over that of the respective uncoated substrate. Titanium substrates coated with titanium spinulose coating formed from a titanium plasma deposited at an angle of θc=0° with a θs of 0°, however, showed growth inhibition of the human umbilical artery endothelial cells (see FIG. 10) over that of the respective uncoated substrate.

Example 5

Effect of Deposition Angle on Spinulose Coating

Silicon (1 cm² by 0.04 cm, single crystal (100) wafer (Encompass Distribution Services, LLC) substrates were cleaned by blowing compressed air over the surface of the substrates before placing in chamber. 316L stainless steel substrates (160 cm²×0.1 cm), mirror polished (McMaster-Carr) were cleaned in an ultrasonic bath, rinsed in deionized water and dried in air. The substrates were placed in the chamber on a floating holder approximately 13 in from the cathode and at a $\theta_C$=0° with a $\theta_S$ ranging from 45° to 80°. Prior to deposition the chamber was pumped to a base pressure of at least 0.088 mPa.

The deposition was carried out in 5 min intervals, with 90 min pauses intervals of no arc current and no gas flow. This deposition-pause cycle was repeated 9 times. A 300 A arc discharge was generated in a background of 160 mPa of argon on a pure titanium (grade 2) cathode (20 in×6 in).

Figure 12:
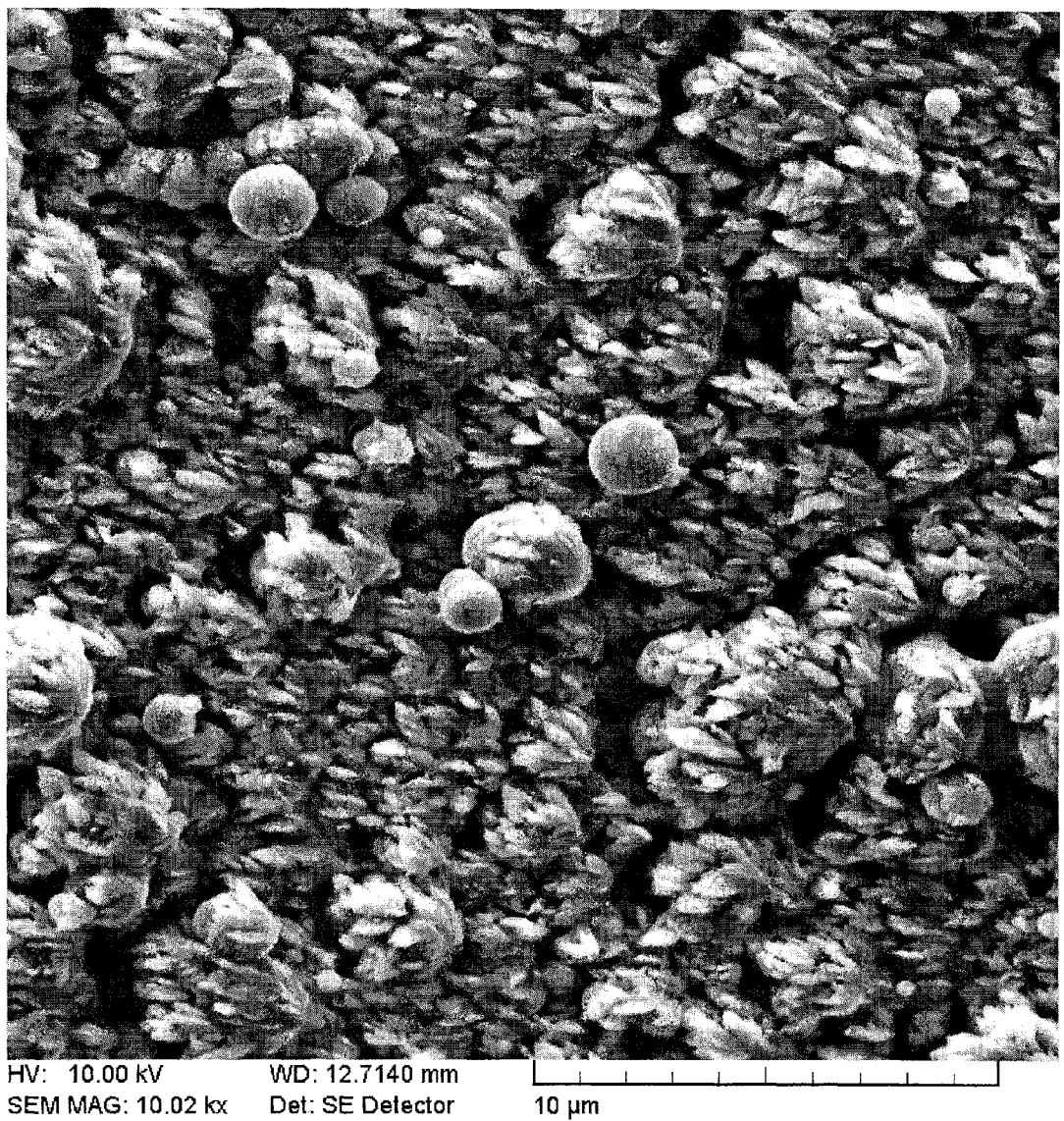
FIG. 12 is a FEG-SEM image of an oblique titanium spinulose coating formed from a titanium plasma deposited at an angle of θc=0° with a θs of 45° on 316L stainless steel.

Samples were imaged in a FEG-SEM (Tescan Mira), operated with an accelerating voltage of 10 kV. The images showed a pronounced oblique angle spinulose morphology (see FIG. 12) with at least 85% of the surface covered by oblique angle spinulose features.

A second batch of coated substrates was prepared as described above with the exception that the deposition protocol did not include intermittent depositions, such that deposition was conducted continuously for 45 min. These coatings exhibited a rounded surface morphology quite distinct from the spinulose coatings and is referred to here as "round" coating (see FIG. 3).

Human osteoblast, human skin fibroblast and human umbilical artery endothelial four hr cell adhesion tests were carried out on 316L stainless steel substrates coated with oblique angle titanium spinulose coating formed from a titanium plasma deposited at an angle of θs=45° with a θc of 0° and compared with cell adhesion on respective substrates coated with titanium spinulose coating formed from a titanium plasma deposited at an angle of θs=0° with a θc of 0°, titanium round coating formed from a titanium plasma deposited at an angle of θs=0° with a θc of 0° and with no coating. Substrates were placed in wells using sterilized tweezers and exposed to UV light for one hr. Each substrate was then rinsed with 2.0 mL of room temperature (1×PBS). The desired amount of room temperature Complete Media (supplemented with FBS and antibiotic) was added to each well. The cells were seeded onto the substrates at 2500 cells/cm$^2$ and incubated at 34° C., 5% $CO_2$ for four hrs. Following incubation, the media and non-adherent cells were removed. The substrates were then rinsed with room temperature (1×PBS) and fixed with 4% paraformaldehyde. The nuclei of adherent cells were fluorescently stained with Hoescht stain and counted using a fluorescent microscope.

Figure 2:
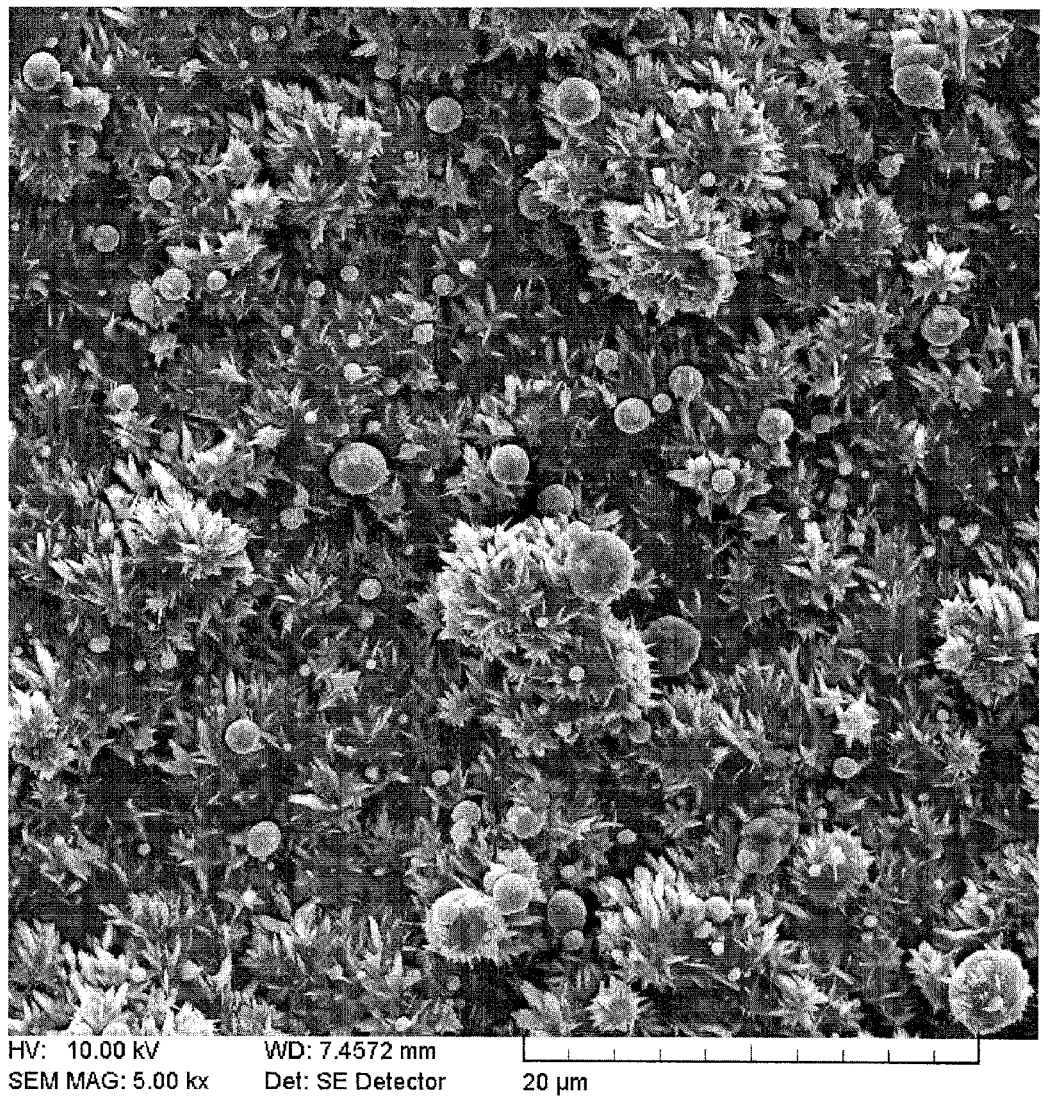
FIG. 2 is a FEG-SEM image of a titanium spinulose coating formed from a titanium plasma deposited at an angle of θc=0° with a θs of 0° on 316L stainless steel.
Figure 13:
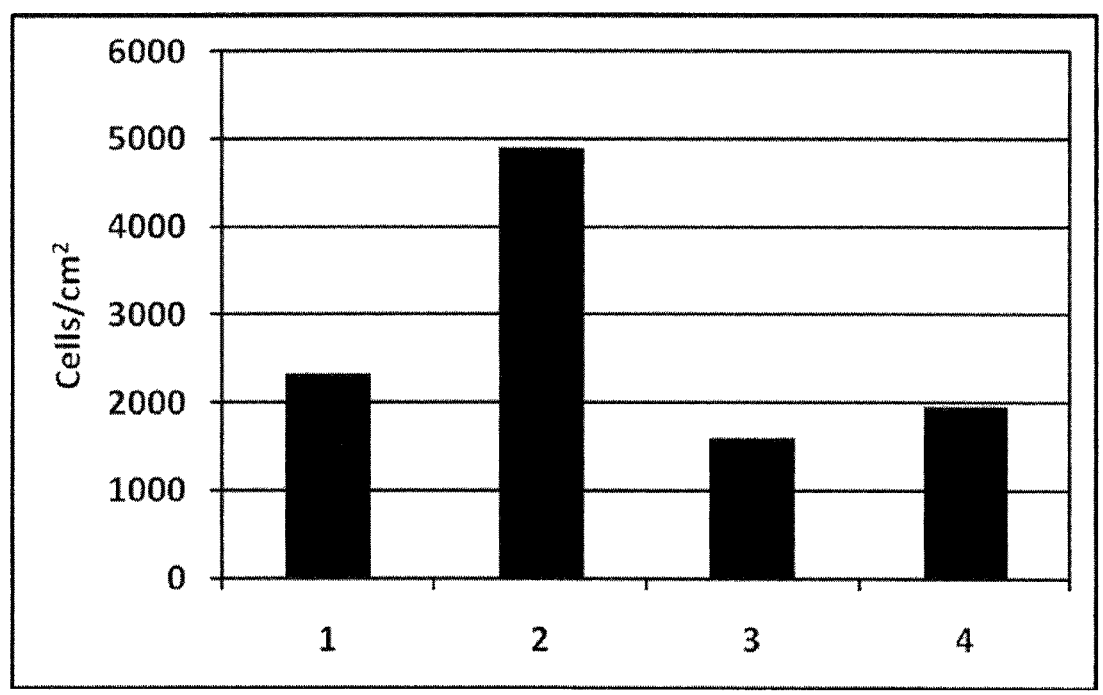
FIG. 13 compares human osteoblast cell adhesion on 316L stainless steel coated with an oblique titanium spinulose coating formed from a titanium plasma deposited at an angle of θc=0° with a θs of 45° (1); titanium spinulose coating formed from a titanium plasma deposited at an angle of θc=0° with a θs of 0° (2); no coating (3); and titanium round coating formed from a titanium plasma deposited at an angle of $\theta_c=0°$ with a θs of 0° (4).
Figure 14:
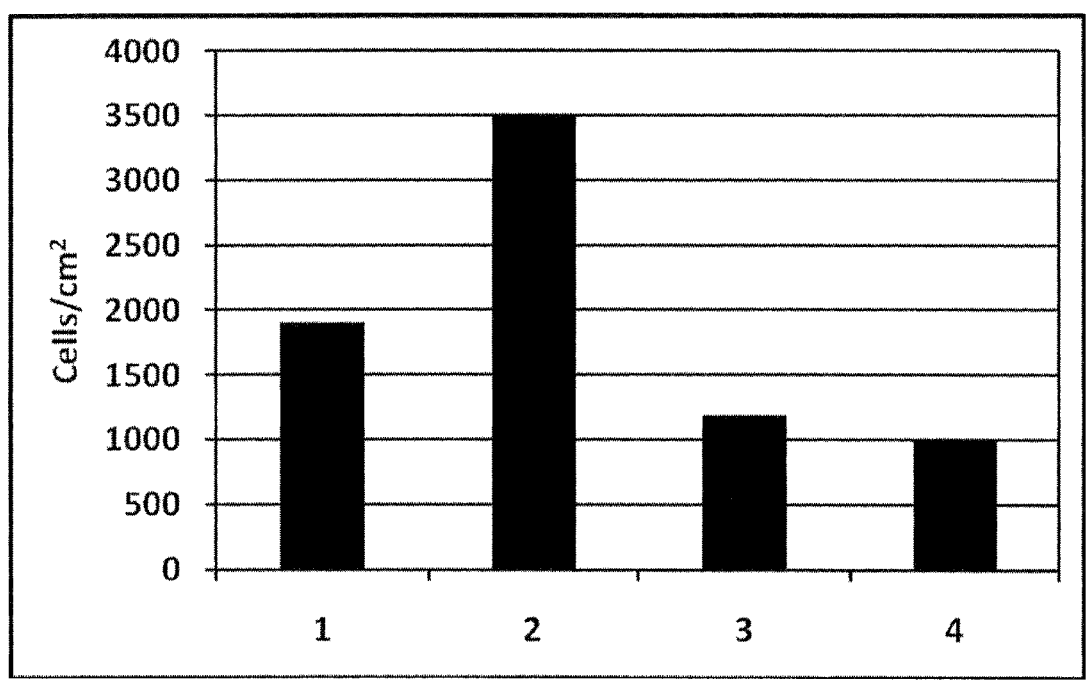
FIG. 14 compares human skin fibroblast cell adhesion on 316L stainless steel coated with an oblique titanium spinulose coating formed from a titanium plasma deposited at an angle of θc=0° with a θs of 45° (1); titanium spinulose coating formed from titanium plasma deposited at an angle of θc=0° with a θs of 0° (2); no coating (3); and a titanium round coating formed from titanium plasma deposited at an angle of θc=0° with a θs of 0° (4).
Figure 15:
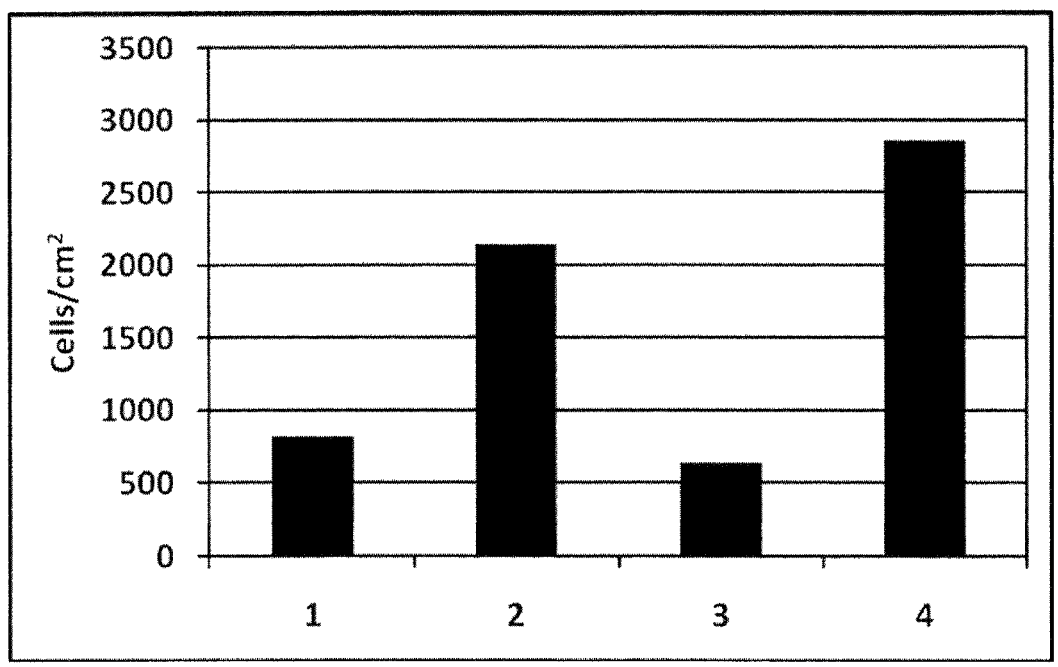
FIG. 15 compares human umbilical artery endothelial cell adhesion on 316L stainless steel coated with an oblique titanium spinulose coating formed from a titanium plasma deposited at an angle of θc=0° with a θs of 45° (1); titanium spinulose coating formed from titanium plasma deposited at an angle of θc=0° with a θs of 0° (2); no coating (3); and a titanium round coating formed from titanium plasma deposited at an angle of θc=0° with a θs of 0° (4).
Figure 16:
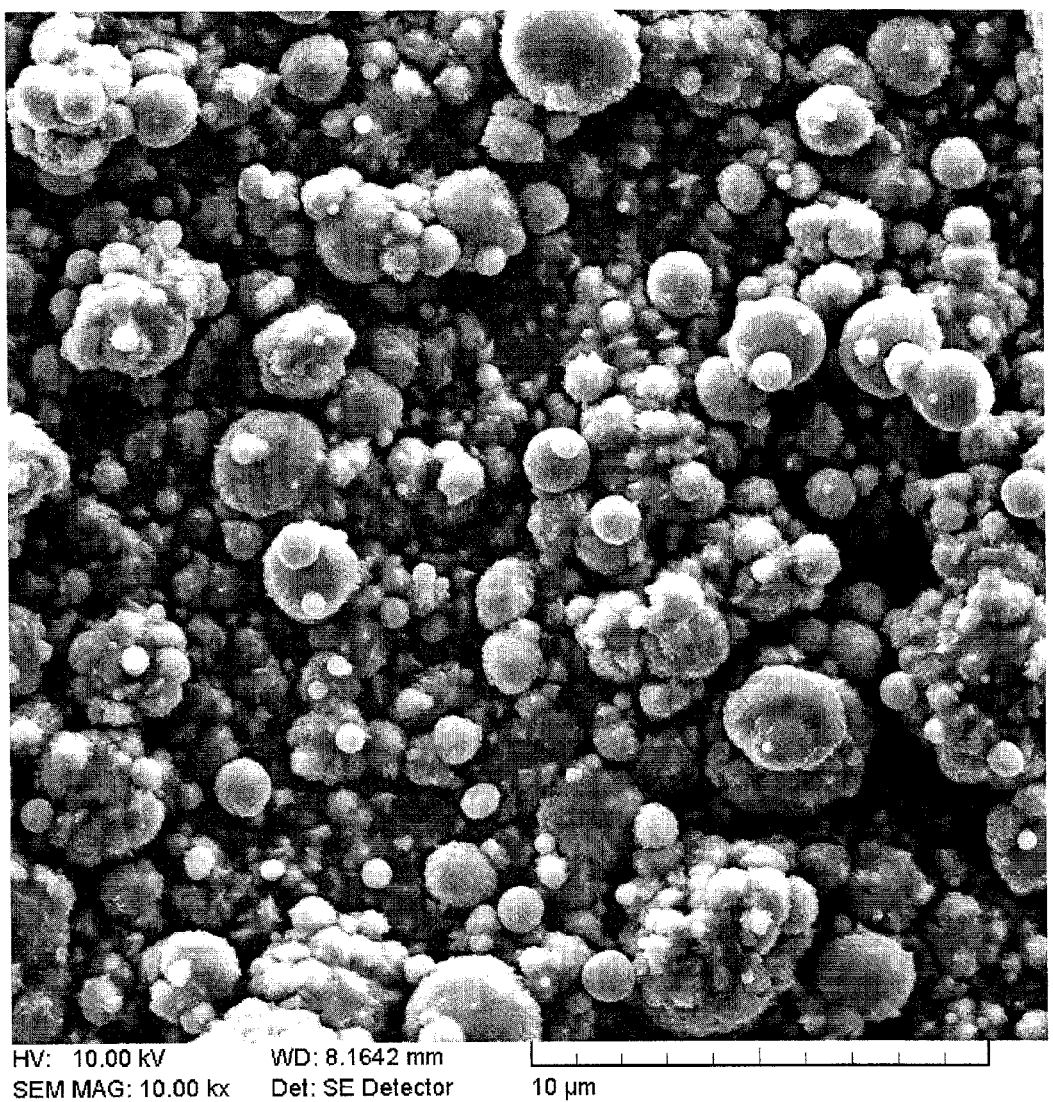
FIG. 16 is a FEG-SEM image of a titanium spinulose coating formed from a titanium plasma deposited at an angle of θc=50° with a θs of 0° on 316L stainless steel.

FIGS. 13, 14 and 15 compare the results of the human osteoblast, human skin fibroblast and human umbilical artery endothelial four hr cell adhesion test on 316L stainless steel coated with an oblique titanium spinulose coating formed from a titanium plasma deposited at an angle of $\theta_S$=45° with a $\theta_C$ of 0°; a titanium spinulose coating formed from a titanium plasma deposited at an angle of $\theta_S$=0° with a $\theta_C$ of 0° (as seen in FIG. 2); uncoated and round coating formed from a titanium plasma deposited at an angle of $\theta_c$=0° with a $\theta_s$ of 0° (FIGS. 3 and 4), respectively. FIGS. 13 and 14 show an increase in the number of human osteoblast and human skin fibroblast cells on the substrates coated with the oblique spinulose coating compared to the respective uncoated and round coated substrates. FIG. 15 shows that for the human umbilical artery endothelial cells, the oblique titanium spinulose coated substrates inhibited the growth of the cells compared to growth on the respective round coated substrates. For all cell types, the spinulose coating formed from a deposition angle of $\theta_S$=0° with a $\theta_C$ of 0° demonstrated an increase in cell adhesion compared to the oblique spinulose coated substrates or to the uncoated substrates.

Example 6

Effect of θc on Titanium Spinulose Coating 316L stainless steel substrates (160 cm$^2$×0.1 cm), mirror polished (McMaster-Carr) were cleaned in an ultrasonic bath, rinsed with deionized water and dried in air. The substrates were placed in the chamber on a floating holder approximately perpendicular to the cathode surface, 8-13 in from the cathode with a $\theta_s$ of 0° to 90° with a $\theta_c$ of 0-80°. Prior to deposition the chamber was pumped to a base pressure of better than 1.45 mPa.

The deposition was carried out in 5 minute intervals, with 90 minute pauses in between of no arc current and no gas flow. The deposition-pause cycle was repeated 9 times. A 200 A arc discharge was generated in a background of 160 mPa of argon on a pure titanium (grade 2) cathode (20×6 in).

Figure 17:
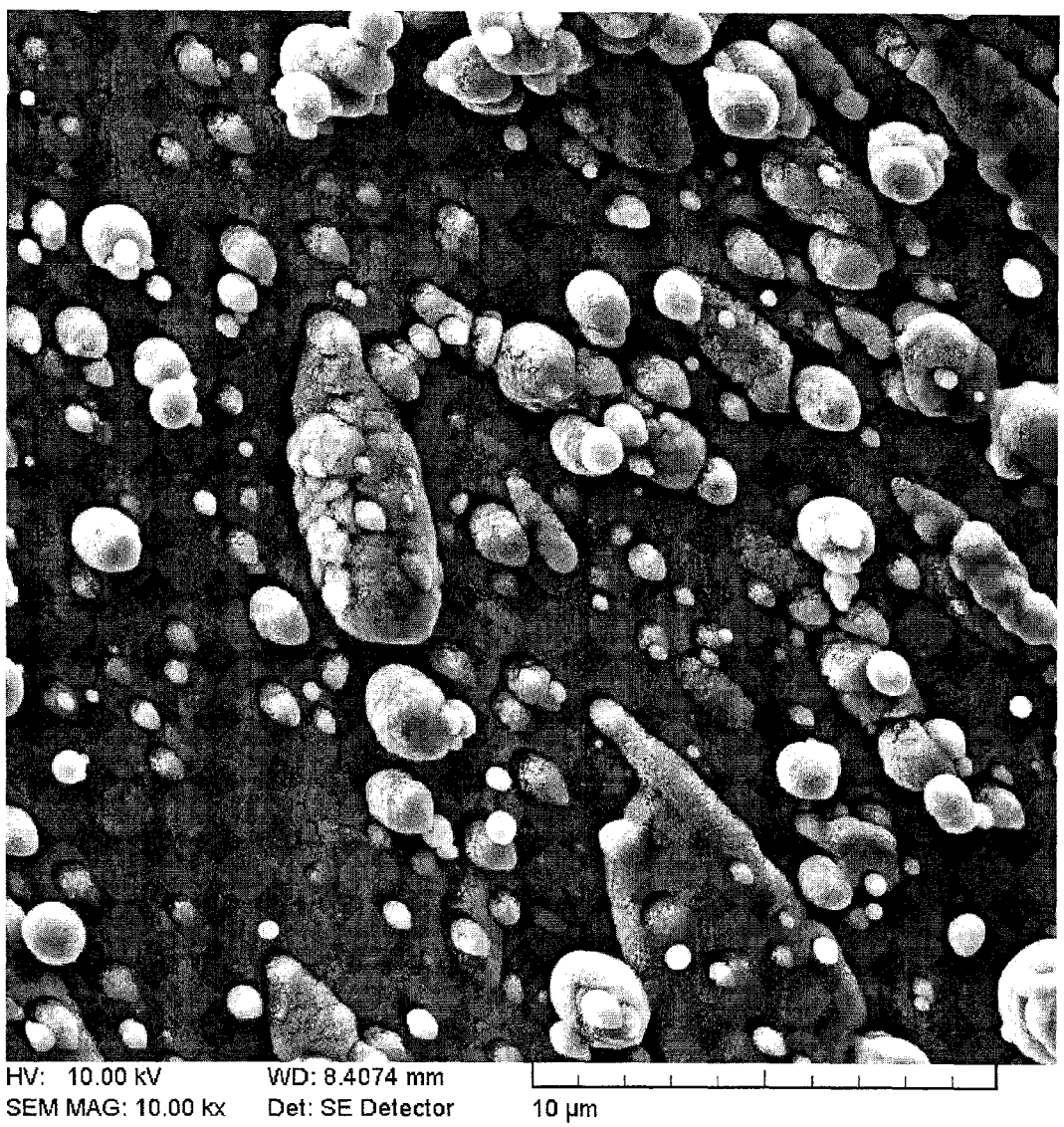
FIG. 17 is a FEG-SEM image of a titanium spinulose coating formed from a titanium plasma deposited at an angle of θc=80° with a θs of 0° on 316L stainless steel.
Figure 18:
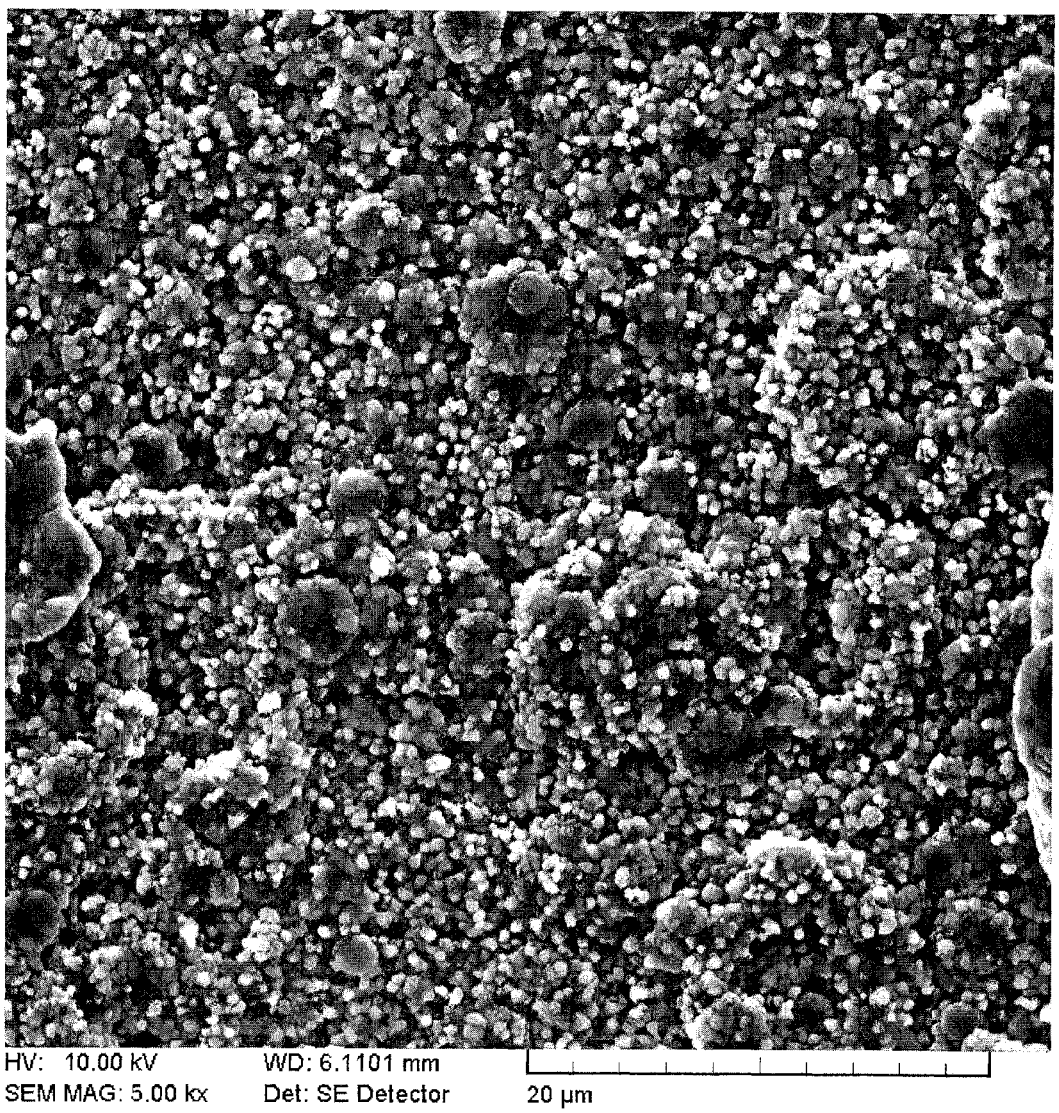
FIG. 18 is a FEG-SEM image of an aluminum geometric coating formed from an aluminum plasma deposited at an angle of θc=0° with a θs of 0° on 316L stainless steel.

Samples were imaged in a FEG-SEM (Tescan Mira), operated with an accelerating voltage of 10 kV. The images showed a spinulose morphology (see FIGS. 2, 17 and 18). As $\theta_C$ approaches 0°, there is a gradual progression in formation of the spinulose morphology.

Example 7

Aluminum Geometric Particle Coating on 316 Stainless Steel 316L stainless steel substrates (160 cm$^2$×0.1 cm) mirror polished (McMaster-Carr) were cleaned in an ultrasonic bath, rinsed with deionized water and dried in hot air. The substrates were placed in the chamber on a floating holder approximately 13 inches away from the cathode at an angle of $\theta_c$=0° with a $\theta_s$ of 0°. Prior to deposition the chamber was pumped to a base pressure of better than 22.7 mPa.

The deposition was carried out in 5 min intervals with 60 min pauses in between of no arc current and no gas flow. The deposition-pause cycle was repeated 3 times. A 150 A arc discharge was generated in a background on 667 mPa of argon on a pure aluminum cathode (4 in×2 in).

Samples were imaged in a FEG-SEM (Tescan Mira), operated with an accelerating voltage of 10 kV. The images showed a pronounced geometric morphology (see FIG. 18).

Human osteoblast, human skin fibroblast and human umbilical artery endothelial cell four hr adhesion tests were carried out on 316L stainless steel substrates coated with aluminum geometric coating formed from an aluminum plasma deposited at an angle of $\theta_c$=0° with a $\theta_s$ of 0° and compared to the respective uncoated substrates. Substrates were placed in wells using sterilized tweezers and exposed to UV light for one hr. Each substrate was then rinsed with 2.0 mL of room temperature (1×PBS). The desired amount of room temperature Complete Media (supplemented with FBS and antibiotic) was added to each well. The cells were seeded onto the substrates at 2500 cells/cm$^2$ and incubated at 34° C., 5% $CO_2$ for four hrs. Following incubation, the media and non-adherent cells were removed. The substrates were then rinsed with room temperature (1×PBS) and fixed with 4% paraformaldehyde. The nuclei of adherent cells were fluorescently stained with Hoescht stain and counted using a fluorescent microscope.

FIGS. 19, 20 and 21 compare the results of the human osteoblast, human skin fibroblast and human umbilical artery endothelial four hour cell adhesion test on 316L stainless steel substrates coated with an aluminum geometric coating formed from aluminum plasma deposited at an angle of $\theta_c$=0° with a $\theta_s$ of 0° and uncoated respectively. FIGS. 19 and 20 show that there was an increase in the number of osteoblasts and endothelial cells attached to the geometric particle coated substrates over that of the uncoated substrates. FIG. 20 shows that the geometric particle coated 316 stainless steel inhibited growth of fibroblast cells to a greater degree than uncoated substrates

REFERENCES

U.S. Pat. No. 5,665,326, Goel and Revankar (Sep. 9, 1997).
Suzuki, M., Nagai, K., Kinoshita, S., Nakajima, K., and Kimura, K., "Vapor phase growth of Al whiskers induced by glancing angle deposition at high temperature" Applied Physics Letters 89, 133103 (2006).
U.S. Pat. Application Pub. No. 2004/0228898 (Ross and Guagliano, Nov. 18, 2004)
Barsoum, M. W., Hoffman, E. N., Doherty, R. D., Gupta, S., and Zavaliangos, A. "Driving force and mechanism for spontaneous metal whisker formation" Phys. Rev. Lett., v. 93(20), 12 Nov. 2004, 206104 (1-4).
Wokulski, Z., "On the microstructure of as-grown TiN whisker-like crystals" Phys. Stat. sol. (a) v. 183(2), 251-60 (2001).
Nolan, T. A., Allard, L. F., Coffey, D. W., Hubbard, C. R., and Padgett, R. A., "Microstructure and crystallography of titanium nitride whiskers grown by a vapor-liquid-solid process", J. Am. Ceram. Soc., v.74(11), 2769-2775 (1991)
Nieto, M. M. and Russell, A. M., "Growth of whiskers due to solid-to-solid phase transformation in zirconium", J. App. Physics, 35, 461 (1964)

Russell, A. M. and Abbott, "Whisker growth from iodide titanium wire", J. App. Physics, 29, 1130 (1958)

What is claimed is:

1. A method for producing a nanorough spinulose titanium (NST) surface comprising:
   depositing titanium by a cyclic nanoplasma deposition process onto a substrate housed within an evacuated chamber;
   stopping plasma discharge and gas flow between cycles for between about 5 to about 810 minutes;
   restarting plasma discharge and gas flow; and
   continuing titanium deposition under initial conditions of deposition for a number of times until a NST surface is formed on said substrate.

2. The method of claim 1 wherein the NST surface is formed on substantially round initially deposited titanium nanoparticles.

3. The method of claim 1 wherein the NST surface comprises pure titanium.

4. The method of claim 1 wherein the depositing is conducted for about 1 min to about 15 min.

5. The method of claim 1 wherein the time between titanium deposition cycles is about 90 min.

6. The method of claim 1 wherein the depositing is continued for about 3 to about 13 cycles.

7. The method of claim 1 wherein the titanium is deposited normal to the substrate surface.

8. The method of claim 1 wherein the titanium is deposited at an angle to the substrate surface.

9. The method of claim 1 wherein the substrate is a metal, metal alloy, polymer or ceramic.

10. The method of claim 9 wherein the substrate is selected from the group consisting of silicone, poly(methylmethacrylate) (PMMA), polyurethane (PU), polyvinyl chloride (PVC), polyethylene terephthalate (PET), polyethylene terephthalate glycol (PETG), polyetheretherketone (PEEK), ultra high molecular weight polyethylene (UHMWPE), and polypropylene (PP).

11. The method of claim 1 wherein the substrate is silicon, glass, carbon, salt, titanium, nitinol, CoCrMo or stainless steel.

12. The method of claim 1 wherein the NST surface comprises spinules ranging in average spike height from about 0.22 μm to about 1.12 μm.

13. The method of claim 12 wherein the spinules have an average spike base width between about 0.3 μm and 0.63 μm.

14. The method of claim 13 wherein the NST surface is about 85% covered with spinules.

* * * * *

UNITED STATES PATENT AND TRADEMARK OFFICE
CERTIFICATE OF CORRECTION

PATENT NO. : 8,158,216 B2
APPLICATION NO. : 11/932831
DATED : April 17, 2012
INVENTOR(S) : Christina Kay Thomas, Luke J. Ryves and Daniel M. Storey Page 1 of 1

It is certified that error appears in the above-identified patent and that said Letters Patent is hereby corrected as shown below:

Column 5,
Line 55, "are control" should read --arc control--.

Signed and Sealed this
Third Day of July, 2012

David J. Kappos
*Director of the United States Patent and Trademark Office*